(12) United States Patent
Meyer et al.

(10) Patent No.: US 12,106,845 B2
(45) Date of Patent: Oct. 1, 2024

(54) CLINICALLY RELEVANT ANONYMIZATION OF PHOTOS AND VIDEO

(71) Applicant: ALIGN TECHNOLOGY, INC., San Jose, CA (US)

(72) Inventors: Eric P. Meyer, Pleasanton, CA (US); Christopher E. Cramer, Durham, NC (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 217 days.

(21) Appl. No.: 17/089,622

(22) Filed: Nov. 4, 2020

(65) Prior Publication Data
US 2021/0134436 A1 May 6, 2021

Related U.S. Application Data

(60) Provisional application No. 62/930,929, filed on Nov. 5, 2019.

(51) Int. Cl.
*G16H 30/20* (2018.01)
*A61B 5/00* (2006.01)
(Continued)

(52) U.S. Cl.
CPC ........... *G16H 30/20* (2018.01); *A61B 5/0088* (2013.01); *G06F 21/6254* (2013.01);
(Continued)

(58) Field of Classification Search
CPC ........ G16H 30/20; G16H 50/50; G16H 50/20; G16H 30/40; G06V 40/171; A61B 5/0088;
(Continued)

(56) References Cited

U.S. PATENT DOCUMENTS

| 5,975,893 A | 11/1999 | Chishti et al. |
| 6,227,850 B1 | 5/2001 | Chishti et al. |

(Continued)

FOREIGN PATENT DOCUMENTS

| EP | 3282379 A1 * | 2/2017 | ............. G06F 19/00 |
| EP | 3451209 A1 * | 8/2017 | ............. G06F 19/00 |

OTHER PUBLICATIONS

GaussianBlur, https://computergraphics.stackexchange.com/questions/39/how-is-gaussian-blur-implemented (Year: 2015).*

(Continued)

*Primary Examiner* — Aryan E Weisenfeld
(74) *Attorney, Agent, or Firm* — FisherBroyles, LLP

(57) ABSTRACT

The disclosed systems and methods for anonymizing clinical data may include receiving representation data corresponding to a body part. The representation data may include a clinically relevant region and an anonymization region. The method may include extracting, from the representation data, clinical representation data corresponding to the clinically relevant region of the representation data and generating artificial representation data corresponding to the anonymization region of the representation data. The method may further include creating, based at least on the clinical representation data and the artificial representation data, anonymized representation data that substantially preserves the clinically relevant region. Various other methods, systems, and computer-readable media are also disclosed.

19 Claims, 9 Drawing Sheets

(51) Int. Cl.
  *G06F 21/62* (2013.01)
  *G06T 11/00* (2006.01)
  *G06V 40/16* (2022.01)
  *G16H 30/40* (2018.01)
  *G16H 50/20* (2018.01)
  *G16H 50/50* (2018.01)

(52) U.S. Cl.
  CPC .......... *G06T 11/001* (2013.01); *G06V 40/171* (2022.01); *G16H 30/40* (2018.01); *G16H 50/20* (2018.01); *G16H 50/50* (2018.01); *G06T 2210/41* (2013.01)

(58) Field of Classification Search
  CPC .......... G06F 21/6254; G06T 11/001; G06T 2210/41
  See application file for complete search history.

(56) References Cited

U.S. PATENT DOCUMENTS

| | | |
|---|---|---|
| 6,227,851 B1 | 5/2001 | Chishti et al. |
| 6,299,440 B1 | 10/2001 | Phan et al. |
| 6,318,994 B1 | 11/2001 | Chishti et al. |
| 6,371,761 B1 | 4/2002 | Cheang et al. |
| 6,386,878 B1 | 5/2002 | Pavlovskaia et al. |
| 6,406,292 B1 | 6/2002 | Chishti et al. |
| 6,409,504 B1 | 6/2002 | Jones et al. |
| 6,457,972 B1 | 10/2002 | Chishti et al. |
| 6,488,499 B1 | 12/2002 | Miller |
| 6,514,074 B1 | 2/2003 | Chishti et al. |
| 6,554,611 B2 | 4/2003 | Chishti et al. |
| 6,582,229 B1 | 6/2003 | Miller et al. |
| 6,602,070 B2 | 8/2003 | Miller et al. |
| 6,621,491 B1 | 9/2003 | Baumrind et al. |
| 6,688,886 B2 | 2/2004 | Hughes et al. |
| 6,726,478 B1 | 4/2004 | Isiderio et al. |
| 6,729,876 B2 | 5/2004 | Chishti et al. |
| 6,739,869 B1 | 5/2004 | Taub et al. |
| 6,767,208 B2 | 7/2004 | Kaza |
| 6,783,360 B2 | 8/2004 | Chishti |
| 7,040,896 B2 | 5/2006 | Pavlovskaia et al. |
| 7,063,532 B1 | 6/2006 | Jones et al. |
| 7,074,038 B1 | 7/2006 | Miller |
| 7,074,039 B2 | 7/2006 | Kopelman et al. |
| 7,077,647 B2 | 7/2006 | Choi et al. |
| 7,108,508 B2 | 9/2006 | Hedge et al. |
| 7,134,874 B2 | 11/2006 | Chishti et al. |
| 7,156,661 B2 | 1/2007 | Choi et al. |
| 7,160,107 B2 | 1/2007 | Kopelman et al. |
| 7,241,142 B2 | 7/2007 | Abolfathi et al. |
| 7,293,988 B2 | 11/2007 | Wen |
| 7,309,230 B2 | 12/2007 | Wen |
| 7,357,634 B2 | 4/2008 | Knopp |
| 7,555,403 B2 | 6/2009 | Kopelman et al. |
| 7,637,740 B2 | 12/2009 | Knopp |
| 7,689,398 B2 | 3/2010 | Cheng et al. |
| 7,736,147 B2 | 6/2010 | Kaza et al. |
| 7,746,339 B2 | 6/2010 | Matov et al. |
| 7,844,356 B2 | 11/2010 | Matov et al. |
| 7,844,429 B2 | 11/2010 | Matov et al. |
| 7,865,259 B2 | 1/2011 | Kuo et al. |
| 7,878,804 B2 | 2/2011 | Korytov et al. |
| 7,880,751 B2 | 2/2011 | Kuo et al. |
| 7,904,308 B2 | 3/2011 | Arnone et al. |
| 7,930,189 B2 | 4/2011 | Kuo |
| 7,942,672 B2 | 5/2011 | Kuo |
| 7,970,627 B2 | 6/2011 | Kuo et al. |
| 7,970,628 B2 | 6/2011 | Kuo et al. |
| 8,038,444 B2 | 10/2011 | Kitching et al. |
| 8,044,954 B2 | 10/2011 | Kitching et al. |
| 8,075,306 B2 | 12/2011 | Kitching et al. |
| 8,092,215 B2 | 1/2012 | Stone-Collonge et al. |
| 8,099,268 B2 | 1/2012 | Kitching et al. |
| 8,108,189 B2 | 1/2012 | Chelnokov et al. |
| 8,126,726 B2 | 2/2012 | Matov et al. |
| 8,260,591 B2 | 9/2012 | Kass et al. |
| 8,275,180 B2 | 9/2012 | Kuo |
| 8,401,826 B2 | 3/2013 | Cheng et al. |
| 8,439,672 B2 | 5/2013 | Matov et al. |
| 8,562,338 B2 | 10/2013 | Kitching et al. |
| 8,591,225 B2 | 11/2013 | Wu et al. |
| 8,788,285 B2 | 7/2014 | Kuo |
| 8,843,381 B2 | 9/2014 | Kuo et al. |
| 8,874,452 B2 | 10/2014 | Kuo |
| 8,896,592 B2 | 11/2014 | Boltunov et al. |
| 8,930,219 B2 | 1/2015 | Trosien et al. |
| 9,037,439 B2 | 5/2015 | Kuo et al. |
| 9,060,829 B2 | 6/2015 | Sterental et al. |
| 9,125,709 B2 | 9/2015 | Matty |
| 9,211,166 B2 | 12/2015 | Kuo et al. |
| 9,220,580 B2 | 12/2015 | Borovinskih et al. |
| 9,364,296 B2 | 6/2016 | Kuo |
| 9,375,300 B2 | 6/2016 | Matov et al. |
| 9,414,897 B2 | 8/2016 | Wu et al. |
| 9,492,245 B2 | 11/2016 | Sherwood et al. |
| 9,642,678 B2 | 5/2017 | Kuo |
| 10,248,883 B2 | 4/2019 | Borovinskih et al. |
| 10,342,638 B2 | 7/2019 | Kitching et al. |
| 10,463,452 B2 | 11/2019 | Matov et al. |
| 10,595,966 B2 | 3/2020 | Carrier, Jr. et al. |
| 10,617,489 B2 | 4/2020 | Grove et al. |
| 10,722,328 B2 | 7/2020 | Velazquez et al. |
| 10,758,322 B2 | 9/2020 | Pokotilov et al. |
| 10,779,718 B2 | 9/2020 | Meyer et al. |
| 10,792,127 B2 | 10/2020 | Kopelman et al. |
| 10,828,130 B2 | 11/2020 | Pokotilov et al. |
| 10,835,349 B2 | 11/2020 | Cramer et al. |
| 10,973,611 B2 | 4/2021 | Pokotilov et al. |
| 10,996,813 B2 | 5/2021 | Makarenkova et al. |
| 10,997,727 B2 | 5/2021 | Xue et al. |
| 2003/0008259 A1 | 1/2003 | Kuo et al. |
| 2003/0143509 A1 | 7/2003 | Kopelman et al. |
| 2003/0207227 A1 | 11/2003 | Abolfathi |
| 2004/0137400 A1 | 7/2004 | Chishti et al. |
| 2004/0152036 A1 | 8/2004 | Abolfathi |
| 2004/0197728 A1 | 10/2004 | Abolfathi et al. |
| 2004/0259049 A1 | 12/2004 | Kopelman et al. |
| 2005/0182654 A1 | 8/2005 | Abolfathi et al. |
| 2005/0244791 A1 | 11/2005 | Davis et al. |
| 2006/0127836 A1 | 6/2006 | Wen |
| 2006/0127852 A1 | 6/2006 | Wen |
| 2006/0127854 A1 | 6/2006 | Wen |
| 2006/0275731 A1 | 12/2006 | Wen et al. |
| 2006/0275736 A1 | 12/2006 | Wen et al. |
| 2008/0306724 A1 | 12/2008 | Kitching et al. |
| 2010/0009308 A1 | 1/2010 | Wen et al. |
| 2010/0068672 A1 | 3/2010 | Arjomand et al. |
| 2010/0068676 A1 | 3/2010 | Mason et al. |
| 2010/0092907 A1 | 4/2010 | Knopp |
| 2010/0167243 A1 | 7/2010 | Spiridonov et al. |
| 2013/0204599 A1 | 8/2013 | Matov et al. |
| 2016/0135925 A1 | 5/2016 | Mason et al. |
| 2016/0242870 A1 | 8/2016 | Matov et al. |
| 2016/0310235 A1 | 10/2016 | Derakhshan et al. |
| 2017/0273760 A1 | 9/2017 | Morton et al. |
| 2018/0168775 A1 | 6/2018 | Derakhshan et al. |
| 2018/0280118 A1 | 10/2018 | Cramer |
| 2019/0029784 A1 | 1/2019 | Moalem et al. |
| 2019/0053876 A1 | 2/2019 | Sterental et al. |
| 2019/0076214 A1 | 3/2019 | Nyukhtikov et al. |
| 2019/0105127 A1 | 4/2019 | Velazquez et al. |
| 2019/0175303 A1 | 6/2019 | Akopov et al. |
| 2019/0192259 A1 | 6/2019 | Kopelman et al. |
| 2019/0328487 A1 | 10/2019 | Levin et al. |
| 2019/0328488 A1 | 10/2019 | Levin et al. |
| 2019/0333622 A1 | 10/2019 | Levin et al. |
| 2019/0343601 A1 | 11/2019 | Roschin et al. |
| 2019/0350680 A1 | 11/2019 | Chekh et al. |
| 2019/0357997 A1 | 11/2019 | Shi et al. |
| 2020/0000551 A1 | 1/2020 | Li et al. |
| 2020/0000552 A1 | 1/2020 | Mednikov et al. |
| 2020/0000554 A1 | 1/2020 | Makarenkova et al. |
| 2020/0000555 A1 | 1/2020 | Yuryev et al. |
| 2020/0085546 A1 | 3/2020 | Li et al. |

(56) References Cited

U.S. PATENT DOCUMENTS

| | | |
|---|---|---|
| 2020/0105028 A1 | 4/2020 | Gao et al. |
| 2020/0107915 A1 | 4/2020 | Roschin et al. |
| 2020/0155274 A1 | 5/2020 | Pimenov et al. |
| 2020/0214800 A1 | 7/2020 | Matov et al. |
| 2020/0297458 A1 | 9/2020 | Roschin et al. |
| 2020/0306011 A1 | 10/2020 | Chekhonin et al. |
| 2020/0306012 A1 | 10/2020 | Roschin et al. |
| 2020/0315744 A1 | 10/2020 | Cramer |
| 2020/0360109 A1 | 11/2020 | Gao et al. |
| 2021/0073998 A1 | 3/2021 | Brown et al. |

OTHER PUBLICATIONS https://www.cancer.gov/publications/dictionaries/cancer-terms/def/oral-cavity, Definition of Oral Cavity (Year: 2023).*
Maximov et al. "CIAGAN: Conditional Identity Anonymization Generative Adversarial Networks" (Year: 2020).*
Maximov (Year: 2020).*
Chhabra N., "Generative Adversarial Networks for Image Anonymization", Master Thesis, Oct. 17, 2019, pp. 1-60, XP055681759.

* cited by examiner

CLINICALLY RELEVANT ANONYMIZATION OF PHOTOS AND VIDEO

RELATED APPLICATIONS

This application claims the benefit under 35 U.S.C. § 119(e) of U.S. Provisional Patent Application No. 62/930,929, filed Nov. 5, 2019, and titled "CLINICALLY RELEVANT ANONYMIZATION OF PHOTOS AND VIDEO," which is incorporated, in its entirety, by this reference.

BACKGROUND

Prior approaches to removing personally identifying patient information from confidential patient data can be less than ideal in at least some respects. Many countries require that medical records comply with standards to protect patient data, such as the Health Insurance Portability and Accountability Act ("HIPAA") in the United States and the General Data Protection Regulations ("GDPR") in the European Union. These standards can require that personally identifiable information be removed prior to making patient data such as patient images publicly available. Treatment professionals such as physicians may wish to share treatment information with other treatment professionals in order to disseminate knowledge with respect to patient care and best practices, for example at conferences. In order to present such patient data publicly, personally identifiable information should typically be removed, but the prior approaches can result in less than complete patient images and images that appear unnatural.

Prior to performing a medical treatment, a medical professional may record or otherwise capture visual data of a patient's clinically relevant areas. For example, a treatment professional may take pictures of the patient's mouth and face. In some instances, the treatment professional may wish to confer with other treatment professionals (e.g., specialists such as orthodontists, oral surgeons, periodontists, and/or general dentists) over possible treatment approaches or present case studies publicly. The treatment professional may share the pictures of the patient with other treatment professionals to discuss treatments. In some instances, it may be desirable to keep certain patient data, such as patient-identifiable information, from other treatment professionals. Additionally, some regulations and laws may require privacy standards regarding patient information as noted above. However, some data, such as photos showing the patient's face, may be fundamentally identifiable.

Conventionally, patient images may be rendered unidentifiable by masking, blanking or otherwise obscuring portions of patients' faces, such as eyes and noses. For example, a portion of the patients' faces such as the eyes can be blacked out. Alternatively, the patient images may be cropped to remove patient-identifiable features. Although effective in maintaining patient anonymity, these blacked out or cropped images may be unattractive and aesthetically less than ideal, may distract from the clinical conditions, and may obscure potentially relevant clinical information. Prior approaches typically remove information from the images and/or videos without replacing the removed information with realistic looking images. The resulting images may appear artificial and modified and can be less aesthetically pleasing than would be ideal in at least some instances.

The present disclosure, therefore, identifies and addresses a need for systems and methods for anonymizing clinical data that preserves the clinically relevant portions while providing anonymized clinical data that appears more realistic.

SUMMARY

As will be described in greater detail below, the present disclosure describes various systems and methods for anonymizing clinical data. Representation data of a patient's body part may be used to construct an artificial version of the body part, which retains the clinically relevant information from the original representation data. By generating artificial representation data and preserving clinical representation data, the systems and methods described herein may create anonymized representation data that provides an aesthetic representation with clinical relevance. The systems and methods described herein may improve anonymization of clinical data by replacing patient-identifiable representation data with artificial representation data, when compared to conventional approaches which merely redact patient-identifiable representation data. In some embodiments, the artificial representation data comprises a photo-realistic image or a series of photo-realistic images in order to provide a more realistic looking image or series of images comprising both the artificial representation data and the clinical representation data while maintaining patient privacy.

In addition, the systems and methods described herein may improve the functioning of a computing device by decomposing the representation data into components as inputs to generating artificial representation data, thereby improving processing efficiency of the computing device as well as allow the computing device to generate more realistic representation data. These systems and methods may also improve the field of data privacy by preserving important information and replacing patient-identifiable information to maintain a whole representation.

INCORPORATION BY REFERENCE

All patents, applications, and publications referred to and identified herein are hereby incorporated by reference in their entirety, and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which.

DETAILED DESCRIPTION

The following detailed description and provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

As used herein, the term "clinical data" may refer to data generated in the process of treating a patient. For example, clinical data may include, without limitation, patient medical information (e.g., dental or other medical information) such as x-rays, two and/or three-dimensional models of a patient's mouth, and/or digital and/or analog pictures of the patient's teeth. Clinical data may also include prescription notes, treatment professional comments, and/or other information relating to a treatment plan.

As used herein, the term "representation data" may refer to any type or form of data which corresponds to or otherwise represents one or more body parts. Representation data may include any clinical data as well as media data. Examples of representation data include, without limitation, a single, still, two-dimensional (2D) image, a photograph, a single, still three-dimensional (3D) model, a series of 2D images which may be frames of a video, a series of posed, deformable 3D models, 3D tomography images, intraoral scanner data, point clouds, 3D point clouds, Digital Imaging and Communications in Medicine (DICOM) images, or other types of visual data. Representation data may also include textual and/or numerical descriptions and/or models of the corresponding body parts.

Figure 1:
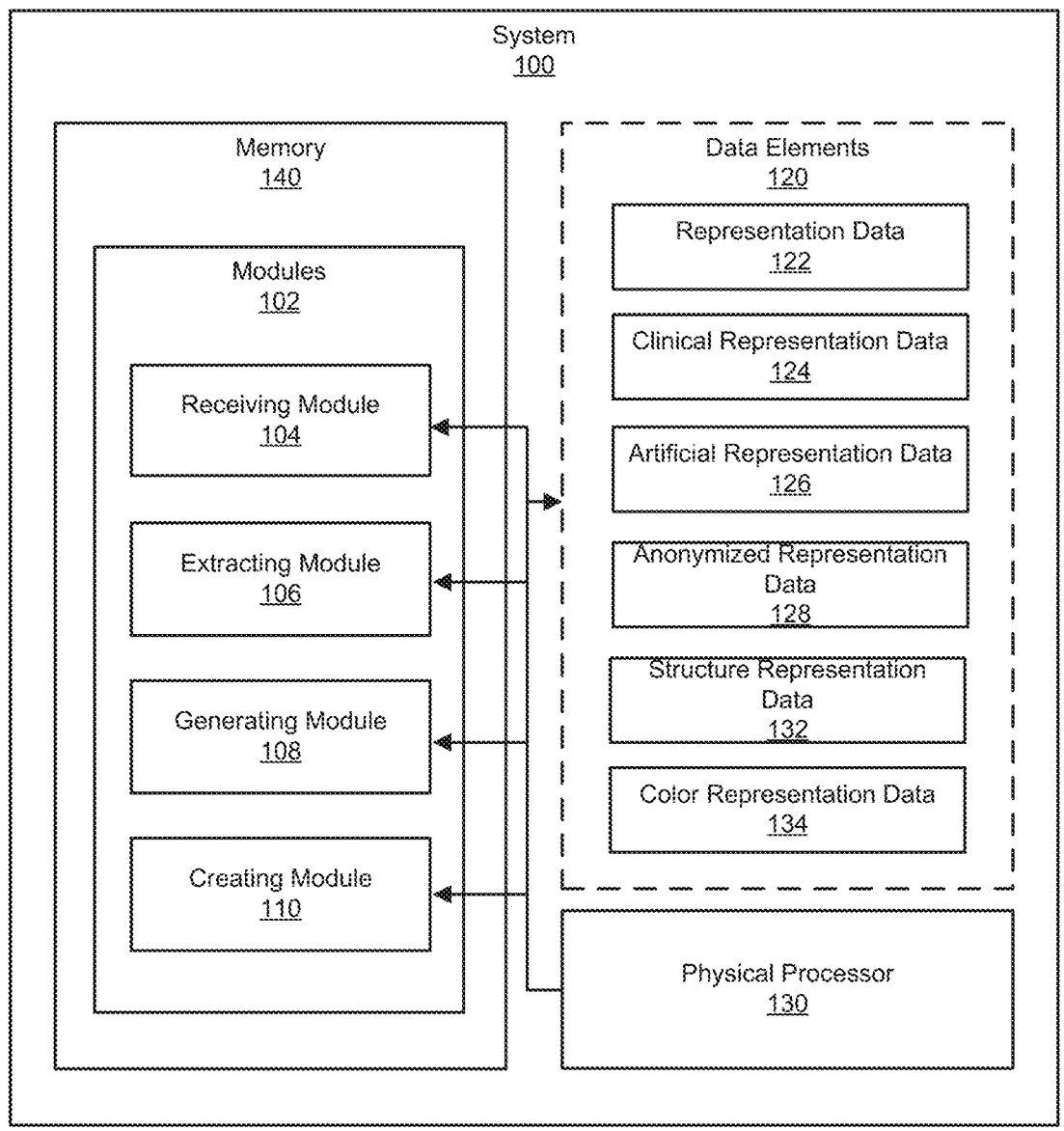
FIG. 1 shows a block diagram of an example system for anonymizing clinical data, in accordance with some embodiments.
Figure 2:
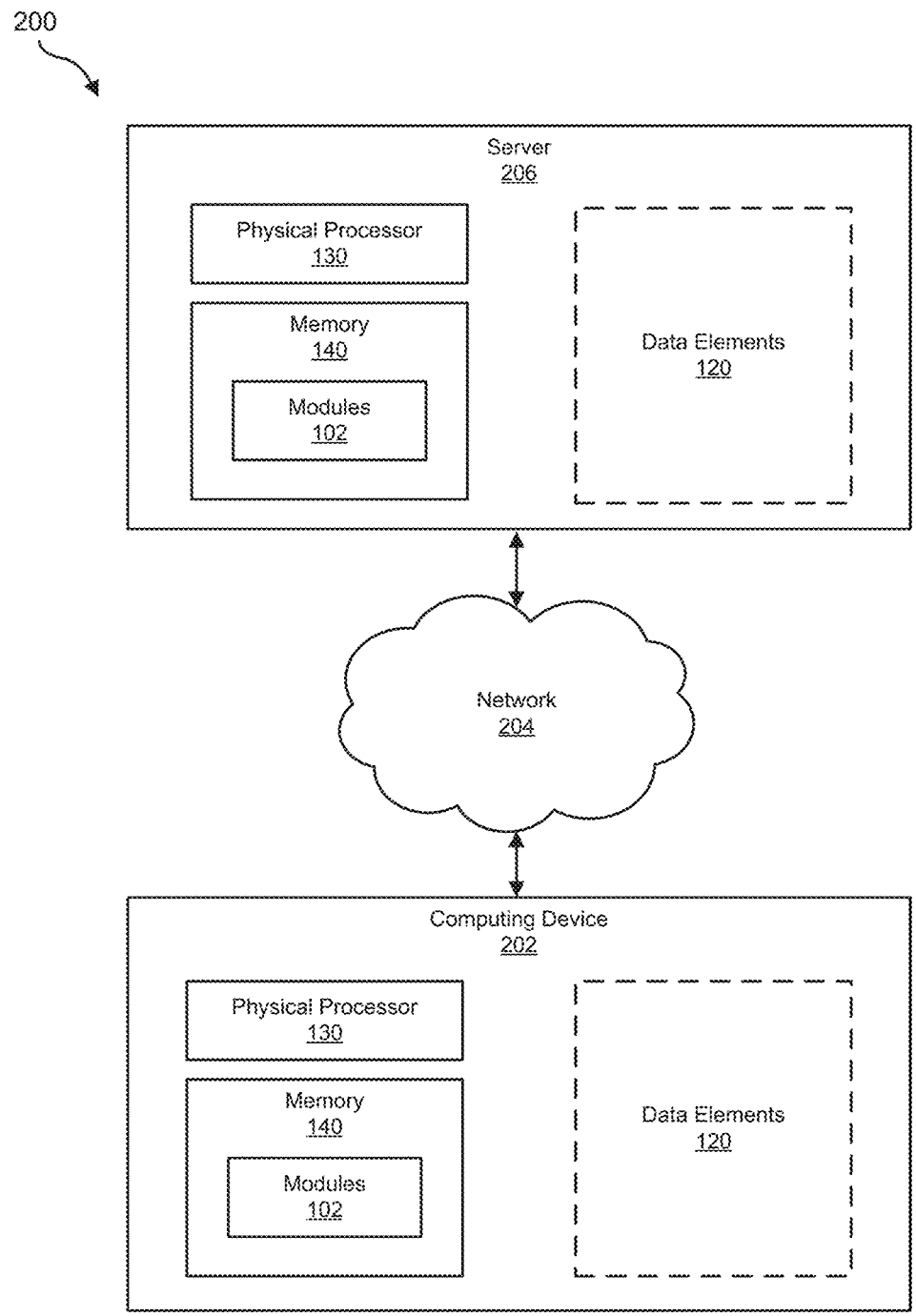
FIG. 2 shows a block diagram of an additional example system for anonymizing clinical data, in accordance with some embodiments.

The following will provide, with reference to FIGS. 1-2, detailed descriptions of example systems for anonymizing clinical data. Detailed descriptions of corresponding computer-implemented methods will also be provided in connection with FIG. 3. Detailed descriptions of example key points will be provided in connection with FIG. 4. Detailed descriptions of additional methods for anonymizing clinical data will also be provided in connection with FIG. 5A, FIG. 5B, and FIG. 6. In addition, detailed descriptions of an example computing system and network architecture capable of implementing one or more of the embodiments described herein will be provided in connection with FIGS. 7 and 8, respectively.

FIG. 1 is a block diagram of an example system 100 for anonymizing clinical data. As illustrated in this figure, example system 100 may include one or more modules 102 for performing one or more tasks. As will be explained in greater detail below, modules 102 may include a receiving module 104, an extracting module 106, a generating module 108, and a creating module 110. Although illustrated as separate elements, one or more of modules 102 in FIG. 1 may represent portions of a single module or application.

In certain embodiments, one or more of modules 102 in FIG. 1 may represent one or more software applications or programs that, when executed by a computing device, may cause the computing device to perform one or more tasks. For example, and as will be described in greater detail below, one or more of modules 102 may represent modules stored and configured to run on one or more computing devices, such as the devices illustrated in FIG. 2 (e.g., computing device 202 and/or server 206). One or more of modules 102 in FIG. 1 may also represent all or portions of one or more special-purpose computers configured to perform one or more tasks.

As illustrated in FIG. 1, example system 100 may also include one or more memory devices, such as memory 140. Memory 140 generally represents any type or form of volatile or non-volatile storage device or medium capable of storing data and/or computer-readable instructions. In one example, memory 140 may store, load, and/or maintain one or more of modules 102. Examples of memory 140 include, without limitation, Random Access Memory (RAM), Read Only Memory (ROM), flash memory, Hard Disk Drives (HDDs), Solid-State Drives (SSDs), optical disk drives, caches, variations or combinations of one or more of the same, and/or any other suitable storage memory.

As illustrated in FIG. 1, example system 100 may also include one or more physical processors, such as physical processor 130. Physical processor 130 generally represents any type or form of hardware-implemented processing unit capable of interpreting and/or executing computer-readable instructions. In one example, physical processor 130 may access and/or modify one or more of modules 102 stored in memory 140. Additionally or alternatively, physical processor 130 may execute one or more of modules 102 to facilitate anonymizing clinical data. Examples of physical processor 130 include, without limitation, microprocessors, microcontrollers, Central Processing Units (CPUs), Field-Programmable Gate Arrays (FPGAs) that implement soft-core processors, Application-Specific Integrated Circuits (ASICs), portions of one or more of the same, variations or combinations of one or more of the same, and/or any other suitable physical processor.

As illustrated in FIG. 1, example system 100 may also include one or more data elements 120, such as representation data 122, clinical representation data 124, artificial representation data 126, anonymized representation data 128, structure representation data 132, and color representation data 134. Data elements 120 generally represent any type or form of representation data and permutations thereof, as will be described further below.

Example system 100 in FIG. 1 may be implemented in a variety of ways. For example, all or a portion of example system 100 may represent portions of example system 200 in FIG. 2. As shown in FIG. 2, system 200 may include a computing device 202 in communication with a server 206 via a network 204. In one example, all or a portion of the functionality of modules 102 may be performed by computing device 202, server 206, and/or any other suitable computing system. As will be described in greater detail below, one or more of modules 102 from FIG. 1 may, when executed by at least one processor of computing device 202 and/or server 206, enable computing device 202 and/or server 206 to anonymize clinical data. For example, and as will be described in greater detail below, one or more of modules 102 may cause computing device 202 and/or server 206 to recite steps of method claim using FIG. 2.

Computing device 202 generally represents any type or form of computing device capable of reading computer-executable instructions. Computing device 202 may be a user device, such as a desktop computer or mobile device. Additional examples of computing device 202 include, without limitation, laptops, tablets, desktops, servers, cellular phones, Personal Digital Assistants (PDAs), multimedia players, embedded systems, wearable devices (e.g., smart watches, smart glasses, etc.), smart vehicles, smart packaging (e.g., active or intelligent packaging), gaming consoles, so-called Internet-of-Things devices (e.g., smart appliances, etc.), variations or combinations of one or more of the same, and/or any other suitable computing device.

Server 206 generally represents any type or form of computing device that is capable of storing and/or processing clinical data. Additional examples of server 206 include, without limitation, security servers, application servers, web servers, storage servers, and/or database servers configured to run certain software applications and/or provide various security, web, storage, and/or database services. Although illustrated as a single entity in FIG. 2, server 206 may include and/or represent a plurality of servers that work and/or operate in conjunction with one another.

Network 204 generally represents any medium or architecture capable of facilitating communication or data transfer. In one example, network 204 may facilitate communication between computing device 202 and server 206. In this example, network 204 may facilitate communication or data transfer using wireless and/or wired connections. Examples of network 204 include, without limitation, an intranet, a Wide Area Network (WAN), a Local Area Network (LAN), a Personal Area Network (PAN), the Internet, Power Line Communications (PLC), a cellular network (e.g., a Global System for Mobile Communications (GSM) network), portions of one or more of the same, variations or combinations of one or more of the same, and/or any other suitable network.

Figure 3:
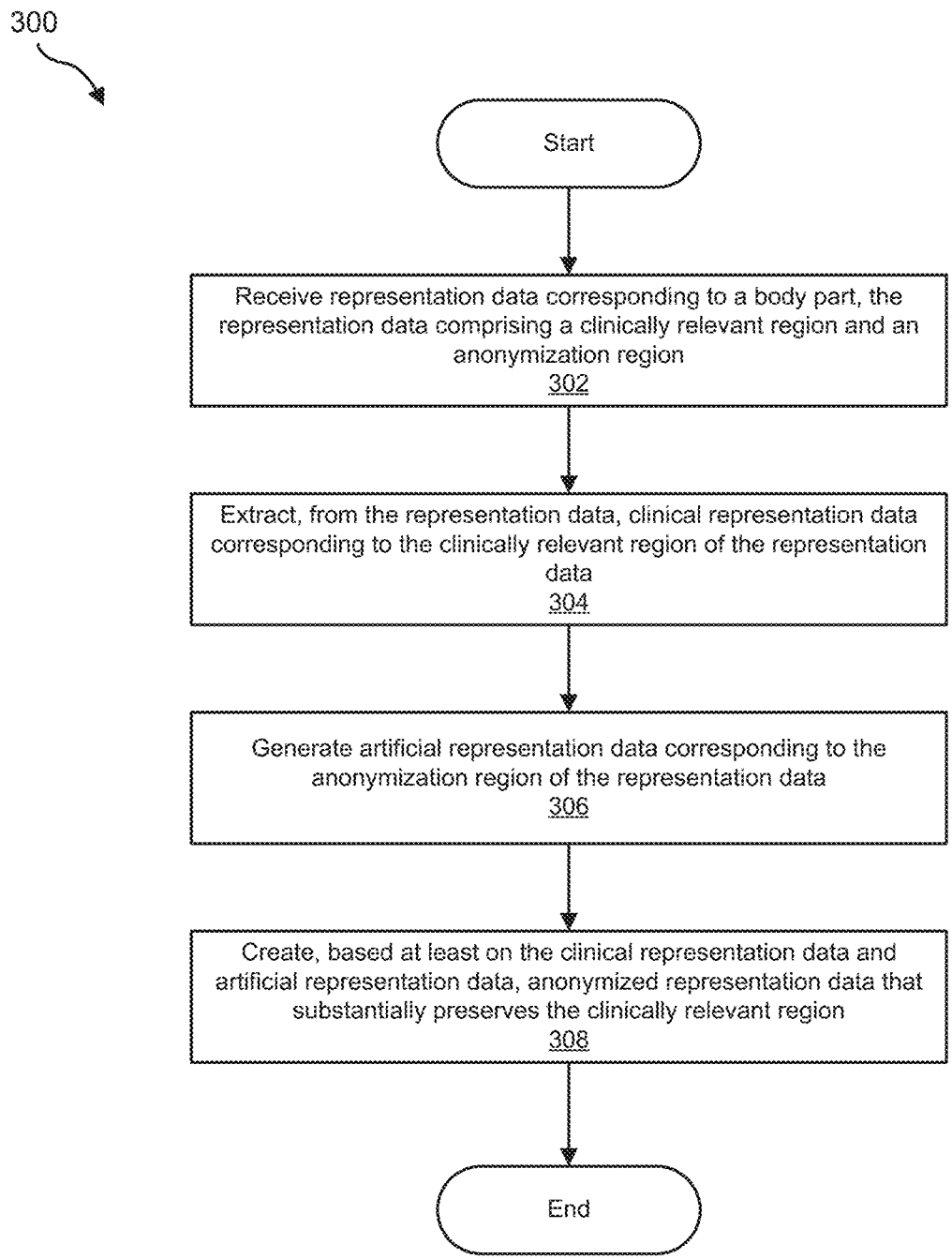
FIG. 3 shows a flow diagram of an example method for anonymizing clinical data, in accordance with some embodiments.

FIG. 3 is a flow diagram of an example computer-implemented method 300 for anonymizing clinical data. The steps shown in FIG. 3 may be performed by any suitable computer-executable code and/or computing system, including system 100 in FIG. 1, system 200 in FIG. 2, and/or variations or combinations of one or more of the same. In one example, each of the steps shown in FIG. 3 may represent an algorithm whose structure includes and/or is represented by multiple sub-steps, examples of which will be provided in greater detail below.

As illustrated in FIG. 3, at step 302 one or more of the systems described herein may receive representation data corresponding to a body part. The representation data may comprise a clinically relevant region and an anonymization region. For example, receiving module 104 may, as part of computing device 202 in FIG. 2, receive representation data 122.

Representation data 122 may include image data of a patient's body part. For instance, representation data 122 may include photos and/or videos of the patient's body captured with an optical sensor such as a camera, stereoscopic camera, etc. Representation data 122 may include other sensor data, such as infrared sensor data, point clouds (e.g., in relation to 3D laser scanning), heat maps, etc. which may describe or otherwise define physical characteristics and structure of the body part.

Representation data 122 may correspond to the patient's entire body. Alternatively, representation data 122 may be more focused on specific body regions and/or parts. Representation data 122 may correspond to various states or milestones before, during, and/or after treatment. For example, representation data 122 may include photos of the body part before, during, and/or after treatment.

In some implementations, representation data 122 may rely on further processing. For instance, representation data 122 may include raw sensor data, such as optical sensor data that may be converted, transformed, merged, etc. In some implementations, receiving module 104 may, as part of server 206, receive representation data 122, such as from computing device 202.

The clinically relevant region may correspond to a region of the patient's body part that exhibit issues to be corrected or otherwise addressed by treatment. The clinically relevant region may be directly or indirectly affected by the treatment. The clinically relevant region may be examined by the treatment professional to develop the proper treatment for the patient.

The anonymization region may correspond to a region of the patient's body part that may include features that may identify the patient. In some implementations, the anonymization region may be defined as regions of the body part that are not included in the clinically relevant region.

In one treatment example, the body part may correspond to the patient's head and face. The clinically relevant region may correspond to the teeth, mouth, and jaws of the patient and the anonymization region may correspond to other portions of the head and face, such as the eyes and nose of the patient.

At step 304, one or more of the systems described herein may extract, from the representation data, clinical representation data corresponding to the clinically relevant region of the representation data. For example, extracting module 106 may, as part of computing device 202 and/or server 206 in FIG. 2, extract clinical representation data 124 from representation data 122.

Clinical representation data 124 may be a subset of representation data 122. For example, when representation data 122 includes image data, clinical representation data 124 may include a sub-image of the image data. Clinical representation data 124 may significantly preserve data from representation data 122 with respect to the clinically relevant region. For instance, clinical representation data 124 may exhibit a fidelity loss of no more than 10% with respect to the clinically relevant region. The fidelity loss may correspond to one or more of an L1 loss, a least absolute deviations (LAD) loss, or a least absolute errors (LAE) loss.

In some implementations, computing device 202 and/or server 206 may extract clinical representation data 124 from representation data 122 by determining key points of the body part from representation data 122. The key points may correspond to distinguishable landmark points of the body part. For instance, when the body part is a face, the key points may correspond to facial landmarks. Extracting module 106 may analyze representation data 122 and label the key points in order to localize various body part features.

Figure 4:
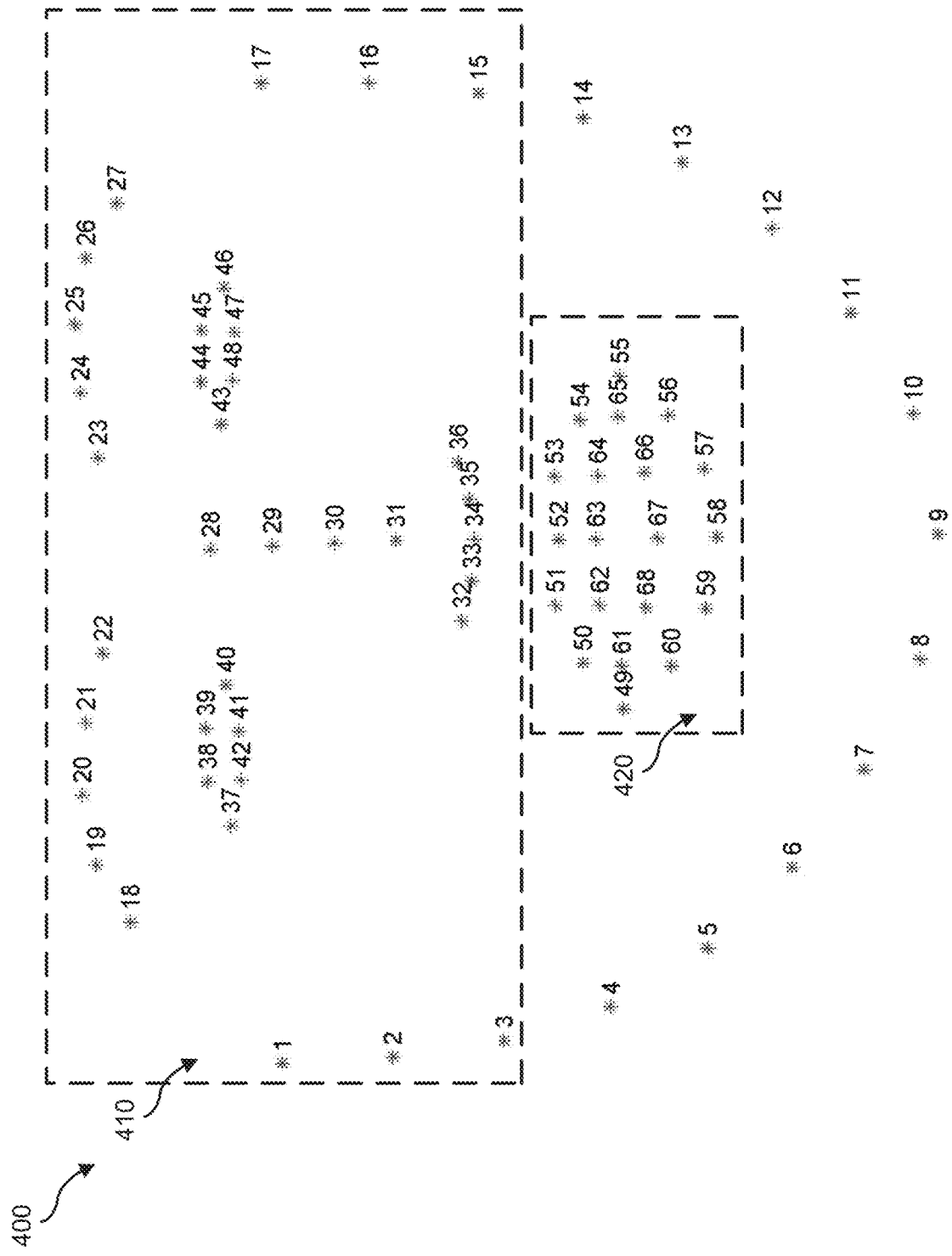
FIG. 4 shows a diagram of landmark features, in accordance with some embodiments.

FIG. 4 illustrates landmark plot 400 corresponding to a patient's face. FIG. 4 shows 68 landmarks, which may correspond to Baumrind landmarks. In other implementations, there may be more or fewer landmarks, such as about 30 to about 150 landmarks. The landmarks may be identified based on regression trees or other approaches, such as deep neural networks for 2D or 3D landmarking.

Once the key points are determined, extracting module 106 may identify key points corresponding to the clinically relevant region. For an oral treatment example, the clinically relevant region may include the patient's mouth. The key points 430 may be landmarks.

The clinically relevant region may correspond to the field of specialty for the treatment professional. For example, the clinically relevant region may be eyes for an optometrist or an ophthalmologist and a nose for a cosmetic surgeon.

The clinically relevant region may include additional body parts and/or relationships therebetween in accordance with a particular issue and/or treatment. For example, when the clinically relevant region is associated with a mandibular advancement treatment, the clinically relevant region may include a pogonion identified. When the clinically relevant region is associated with a cleft lip treatment, the clinically relevant region may include a facial deformity. The facial deformity may be one or more of a cleft lip, cleft palate, facial injury, or dental trauma, for example.

In another example, when the clinically relevant region is associated with a deep bite treatment, the clinically relevant region may include an upper jaw and a lower jaw to encapsulate a relationship between the upper and lower jaws. When the clinically relevant region is associated with a palatal expansion treatment, the clinically relevant region may include a horizontal face width.

In yet another example, when the clinically relevant region is associated with a class II malocclusion treatment, the clinically relevant region may include upper and lower dental archforms. When the clinically relevant region is associated with a midline shift, the clinically relevant region may include a philtrum.

In other examples, when the clinically relevant region is associated with soft tissue changes, the clinically relevant region may include a soft tissue facial landmark. The soft tissue facial landmark may include one or more of a pogonion, a soft tissue end point, or a result of soft tissue analysis.

Some other features may also be included with the clinically relevant region. Patient characteristics, such as gender and/or age, may be included. Age may be categorized, such as a growing patient or a mature patient, or segmented, such as 5 year age segments corresponding to child, teen, young adult, adult, or elderly.

The clinically relevant region may include facial profile information. For instance, a lower facial height measured from the philtrum to the chin, an inter-pupilary distance between the eyes, asymmetry in the nose, corners of the lips, and lip width may be included with the clinically relevant region. Certain other features, such as eye shape, ear position, forehead, and nose size and shape, may be anonymized or otherwise modified.

The clinically relevant region may include side profile information. For instance, a relationship between the upper to lower jaw, a nose prominence, and convexity of the face may be included with the clinically relevant region. Certain other features, such as cheekbones, ears, eyes, and hairstyle may be anonymized or otherwise modified.

In other implementations, the treatment professional may define the clinically relevant region. In yet other implementations, extracting module 106 may diagnose possible conditions, for instance by detecting anomalies with the key points, and automatically select an appropriate clinically relevant region.

Using the identified key points, extracting module 106 may select sub-representation data from representation data 122. FIG. 4 illustrates clinically relevant region 420 which includes the patient's mouth. After extracting module 106 identifies the patient's mouth from the key points, extracting module 106 may use the identified key points to define a sub-region of the body part, such as by expanding a region around the identified key points. For instance, clinically relevant region 420 includes the patient's mouth as well as jaw.

Extracting module 106 may select the sub-representation data to include data corresponding to the defined sub-region. For example, extracting module 106 may, when representation data 122 includes image data, select bounding boxes or masked portions of the image data, corresponding to the defined sub-region, as the sub-representation data. Extracting module 106 may extract the sub-representation data as clinical representation data 124.

FIG. 4 also illustrates anonymization region 410. Anonymization region 410 may include regions of the body part exclusive of clinically relevant region 420. In some implementations, extracting module 106 may actively define anonymization region 410. For instance, extracting module 106 may specifically identify features that may be used to identify patients. In the orthodontic treatment example, in which clinically relevant region 420 may include the patient's mouth, anonymization region 410 may include the patient's eyes.

In some implementations, extracting module 106 may optionally create additional intermediary representations, such as structure representation data 132 and color representation data 134, which may be used for generating artificial representation data 126.

Structure representation data 132 may correspond to a shape and/or pose of the body part. The shape and/or pose may be used for generating a realistic artificial body parts in similar poses. The shape and/or pose may also be used when generating and/or manipulating 3D models of the body part. Structure representation data 132 may include the key points. In some implementations, the key points may be connected.

Although structure representation data 132 corresponds to the body part in its entirety (as represented by representation data 122), in some implementations structure representation data 132 may correspond to a portion of representation data 132, such as anonymization region 410, clinically relevant region 420, and combinations and/or portions thereof.

Extracting module 106 may determine structural representation data 132 using the key points. Extracting module 106 may connect the key points, for instance in accordance to detected body features. In some implementations, extracting module 106 may use contour or edge detection on representation data 122, e.g., when representation data 122 includes image and/or video data.

Color representation data 134 may indicate one or more colors of one or more regions of the body part. Color, such as skin color, hair color, lips, background, etc., may be indicative of patient characteristics, such as race and/or ethnicity. Although skin color may potentially be a patient-identifying feature, in certain instances the patient's race may be clinically relevant information. For example, different races may react differently to certain conditions or treatments. Thus, color representation data 134 may preserve the one or more colors while obscuring a structure of the body part, to mitigate patient identification.

Extracting module 106 may determine color representation data 134 using a Gaussian blur, a piecewise non-linear function, or any other method which preserves colors while obscuring structural features of the body part. For instance, smooth colors may be extracted from various regions of the face.

Returning to FIG. 3, at step 306 one or more of the systems described herein may generate artificial representation data corresponding to the anonymization region of the representation data. For example, generating module 108 may, as part of computing device 202 and/or server 206 in FIG. 2, generate artificial representation data 126.

Artificial representation data 126 may represent an anonymized version of the body part. The anonymized version of the body part, which may include the anonymization region as well as the clinically relevant region, may be a realistic duplicate of the body part having alterations in order to conceal the patient's identity.

Generating module 108 may create artificial representation data 126 in various ways. For instance, generating module 108 may use, when available, structure representation data 132 and/or color representation data 134. Generating module 108 may incorporate structure representation data 132 such that the anonymized body part represented by artificial representation data 126 has a similar structure and/or pose of the original body part. Generating module 108 may incorporate color representation data 134 such that the anonymized body part has a similar color scheme (e.g., similar skin tones).

Artificial representation data 126 may comprise, for example, a photo-realistic image. The anonymization region may be represented by a color image such that the photo-realistic image may include an output color image. The photo-realistic image may be a 2D image. The 2D image may have been generated from 3D data, such as a 3D anonymization region.

Generating module 108 may compare the anonymization region to artificial representation data 126 to confirm sufficient anonymization of artificial representation data 126. For example, artificial representation data may exhibit a fidelity loss of 30% or more with respect to the anonymization region of representation data 122. The fidelity loss of the anonymization region may correspond to one or more of an L1 loss, a least absolute deviations (LAD) loss, or a least absolute errors (LAE) loss.

Artificial representation data 126 may exhibit a contrast of at least 50% between a maximum intensity pixel of artificial representation data 126 and a minimum intensity pixel of artificial representation data 126. For instance, artificial representation data 126 may comprise a plurality of red pixels, a plurality of blue pixels, and a plurality of green pixels. The contrast may comprise at least 50% for each of the plurality of red pixels, the plurality of blue pixels, and the plurality of green pixels.

Alternatively or in addition, the anonymization region may comprise a first power spectrum distribution of spatial frequencies and artificial representation data 126 may comprise a second power spectrum distribution of special frequencies. Work in relation to the present disclosure suggests that a photo realistic artificial representation may comprise spatial frequencies similar to the anonymization region. The first power spectrum distribution of spatial frequencies may comprise a first amount of spectral power between a Nyquist sampling frequency and half of the Nyquist sampling frequency and the second power spectrum distribution may comprise a second amount of spectral power between the Nyquist frequency and half of the Nyquist frequency. The second amount may differ from the first amount by no more than about 50% of the first amount and optionally no more than about 25%.

At step 308, one or more of the systems described herein may create, based at least on the clinical representation data and artificial representation data, anonymized representation data that substantially preserves the clinically relevant region. For example, creating module 110 may, as part of computing device 202 and/or server 206 in FIG. 2, create anonymized representation data 128 based at least on clinical representation data 124 and artificial representation data 126.

Anonymized representation data 128 may correspond to a combination of clinical representation data 124 and artificial representation data 126. Anonymized representation data 128 may provide an aesthetically pleasing, realistic representation of the body part. Because anonymized representation data 128 significantly preserves clinical representation data 124, treatment professionals may use anonymized representation data 128 to accurately diagnose and/or treat the patient. Because anonymized representation data 128 incorporates artificial representation data 126, the patient's identity may remain concealed.

Anonymized representation data 128 may comprise image or video data. Alternatively, anonymized representation data 128 may comprise 3D data, such as 3D models, stereoscopic data, etc.

Creating module 110 may create anonymized representation data 128 in various ways. For instance, creating module 110 may use, when available, structure representation data 132 and/or color representation data 134. In certain implementations, creating module 110 may create anonymized representation data 128 containing video data by creating each frame of the video data as a 2D image. For example, creating module 110 may create, based on at least clinical representation data 124 and artificial representation data 126, a first frame corresponding to the body part in a pose. Creating module 110 may create a second frame corresponding to the body part transitioning the pose to another pose.

Creating module 110 may include a generator for creating representations. The generator may comprise an in-painting tool, such as those based on Bayesian statistics, dictionary building, compressive sensing, etc. Alternatively or in addition, creating module 110 may utilize machine learning techniques, such as a generative adversarial network (GAN), neural networks or other deep learning architectures, and/or other artificial intelligence approaches, to create anonymized representation data 128, as will be discussed further with respect to FIG. 6. Creating module 110 may also use the GAN to enforce temporal coherence between frames created by creating module 110. In other implementations, creating module 110 may use any other appropriate tool for generating representation data.

Figure 5A:
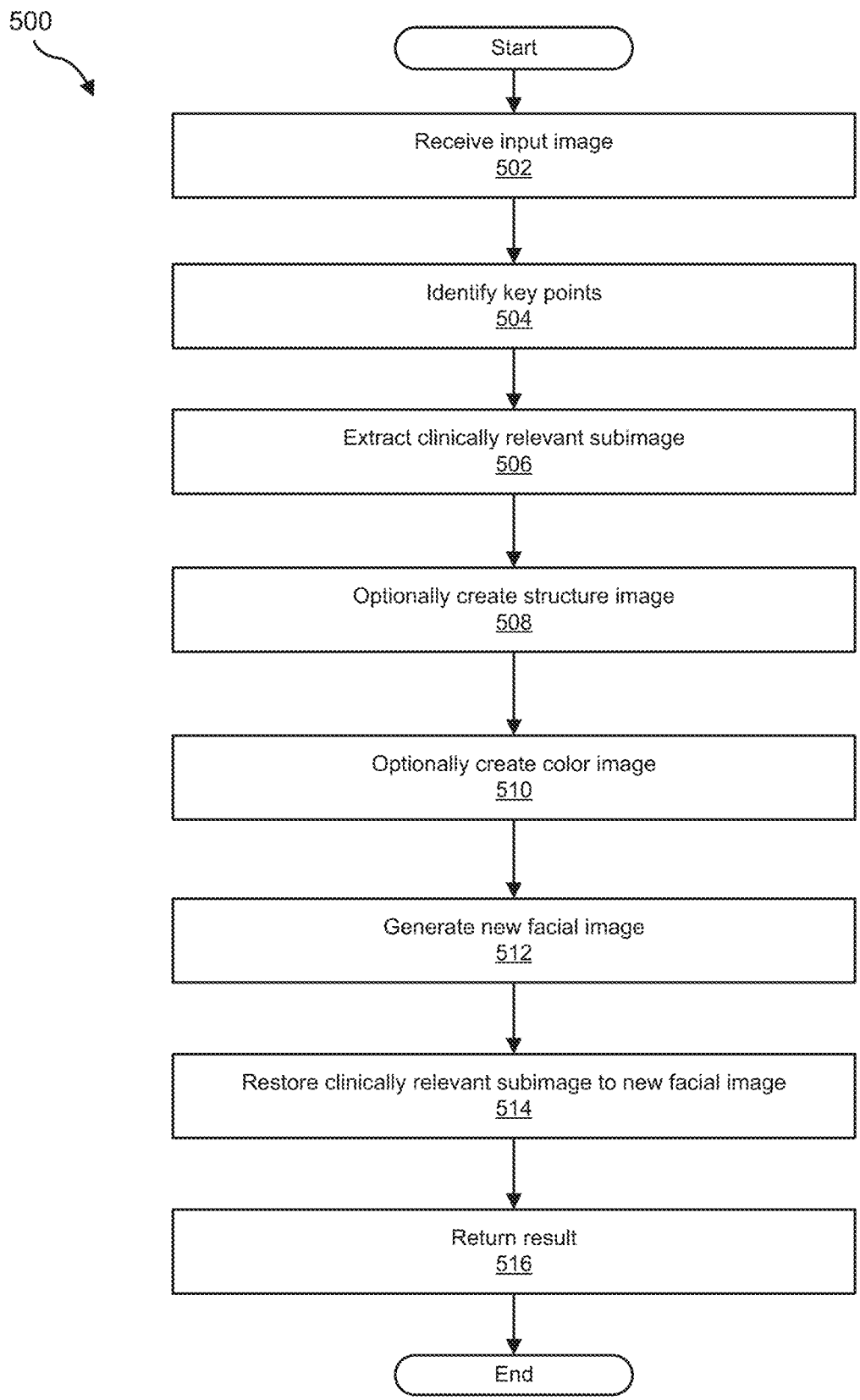
FIG. 5A shows a flow diagram of an additional example method for anonymizing clinical data, in accordance with some embodiments.
Figure 5B:
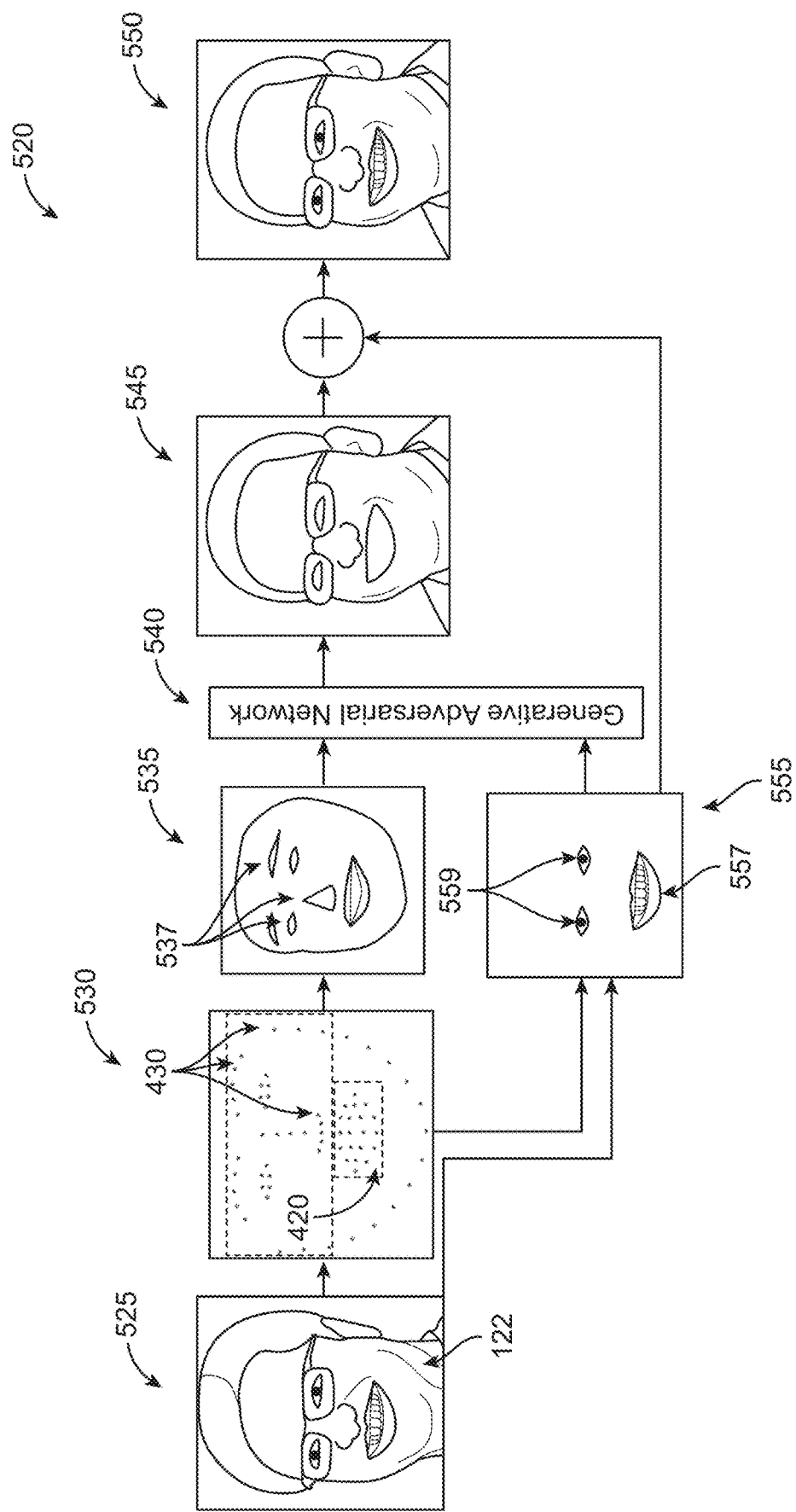
FIG. 5B shows a data flow diagram of an example method for anonymizing clinical data, in accordance with some embodiments.

FIG. 5A is a flow diagram of an example computer-implemented method 500 for anonymizing clinical data and FIG. 5B shows a flow diagram of data in the computer-implemented method 500. The steps shown in FIG. 5A may be performed by any suitable computer-executable code and/or computing system, including system 100 in FIG. 1, system 200 in FIG. 2, and/or variations or combinations of one or more of the same. In one example, each of the steps shown in FIG. 5A may represent an algorithm whose structure includes and/or is represented by multiple sub-steps, examples of which will be provided in greater detail below. Although method 500 is described herein with respect to the orthodontic treatment example, method 500 may be applied to other examples.

As illustrated in FIG. 5A, at step 502 one or more of the systems described herein may receive an input image, such as input image 525. For example, receiving module 104 may, as part of computing device 202 and/or server 206 in FIG. 2, receive representation data 122 from input image 525.

At step 504, one or more of the systems described herein may identify key points 430. For example, extracting module 106 may, as part of computing device 202 and/or server 206 in FIG. 2, identify key points 430 from representation data 122 corresponding to body landmarks. FIG. 5B shows a representation 530 of the key points 430 identified in the input image 525 or representation data 122. The key points 430 may includes key points that identify the eyebrows, eye opening or eyelids, the outline of the face, the jawline, the bridge, apex, nostrils, and ala of the nose, the mount opening, the inside and outside of the lips, At step 506, one or more of the systems described herein may extract a clinically relevant sub-image. For example, extracting module 106 may, as part of computing device 202 and/or server 206 in FIG. 2, extract clinical representation data 124 from representation data 122. FIG. 5B shows a clinically relevant sub image 555 which includes a sub image of the mouth 557 and a sub image of the eyes 559. The sub images may be generated based on the key points. For example, sub image 557 may be generated based on the key points that define one or more of the mouth opening, inner edge of the lips, and the outer edge of the lips. A sub image may be generated based on an geometric shape generated by connecting the key points. In some embodiments, the sub image may include image data that extends beyond the key points or the geometric shape or area generated based on the key points. For example, the sub image may extend 1, 5, 10, 20, 50, or 100 pixels beyond the key points or the geometric shape or area generated based on the key points. In some embodiments, the sub image may extend beyond the key points a distance based on a dimension, such as a length or width of the geometric shape or area generated by the key points. For example, the sub image may extend about or less than about 1, 2, 5, 10, or 15 percent of the maximum liner dimension between two key points of the geometric shape or area generated based on the key points.

At step 508, one or more of the systems described herein may optionally create a structure image. For example, extracting module 106 may, as part of computing device 202 and/or server 206 in FIG. 2, create structure representation data 132 from representation data 122. FIG. 5B shows a structure image 535 generated based on the key points 430. The structure image 535 may include data representing one or more structures 537 of the face. For example, the data 537 may represent the eyebrows, eyes, nose, mouth opening, lips, jawline, and face outline. The data 537 may be based on the key points 430. In some embodiments, the data represents a mask of the various features of a face. For example, data 537 may include a mask of the outline of the face, a mask for the eyebrows, a mask for the eyes, a mask for the nose, a mask for the mouth opening, and a mask for the lips.

At step 510, one or more of the systems described herein may optionally create a color image. For example, extracting module 106 may, as part of computing device 202 and/or server 206 in FIG. 2, create color representation data 134 from representation data 122. A color representation data 134 may include aspects of the color of the image in the representation data. For example, the color representation data 134 may include the colors in the image data 122 and/or clinical representation data 124. In some embodiments, the color representation data 134 may include the colors and the respective locations of the colors in the data 122. In some embodiments, the color representation data 134 may include color of skin about the lips or eyes or color within the clinical data.

At step 512, one or more of the systems described herein may generate a new facial image. For example, generating module 108 may, as part of computing device 202 and/or server 206 in FIG. 2, generate artificial representation data 126 from representation data 122. The generating module may include a GAN, such as GAN 540 of FIG. 5B. In some embodiments, the generate artificial representation data 126 may include image data, such as an image 545 that is generated based on the mask 535. In some embodiments, the image 545 is generated based on the mask 535 and the color data. In some embodiments, the artificial representation data 126 may include data that artificially represents the representation data 122, without the representation data 122.

At step 514, one or more of the systems described herein may restore the clinically relevant sub-image to the new facial image. For example, creating module 110 may, as part of computing device 202 and/or server 206 in FIG. 2, incorporate clinical representation data 124 into artificial representation data 126 to create anonymized representation data 128. The clinical representation data 124 may be incorporated into the artificial representation data 126 based on the mask. For example, the mask may include data related to the relative positions of the artificial representation data 126 and the clinical representation data 124. The creating module 110 may use the relative positions to position clinical representation data 124 relative to the artificial representation data 126 within an image, such as in image 550, which may be the anonymized representation data 128.

As illustrated in FIG. 5A, at step 516 one or more of the systems described herein may return a result. For example, creating module 110 may, as part of computing device 202 and/or server 206 in FIG. 2, display and/or transmit anonymized representation data 128.

Figure 6:
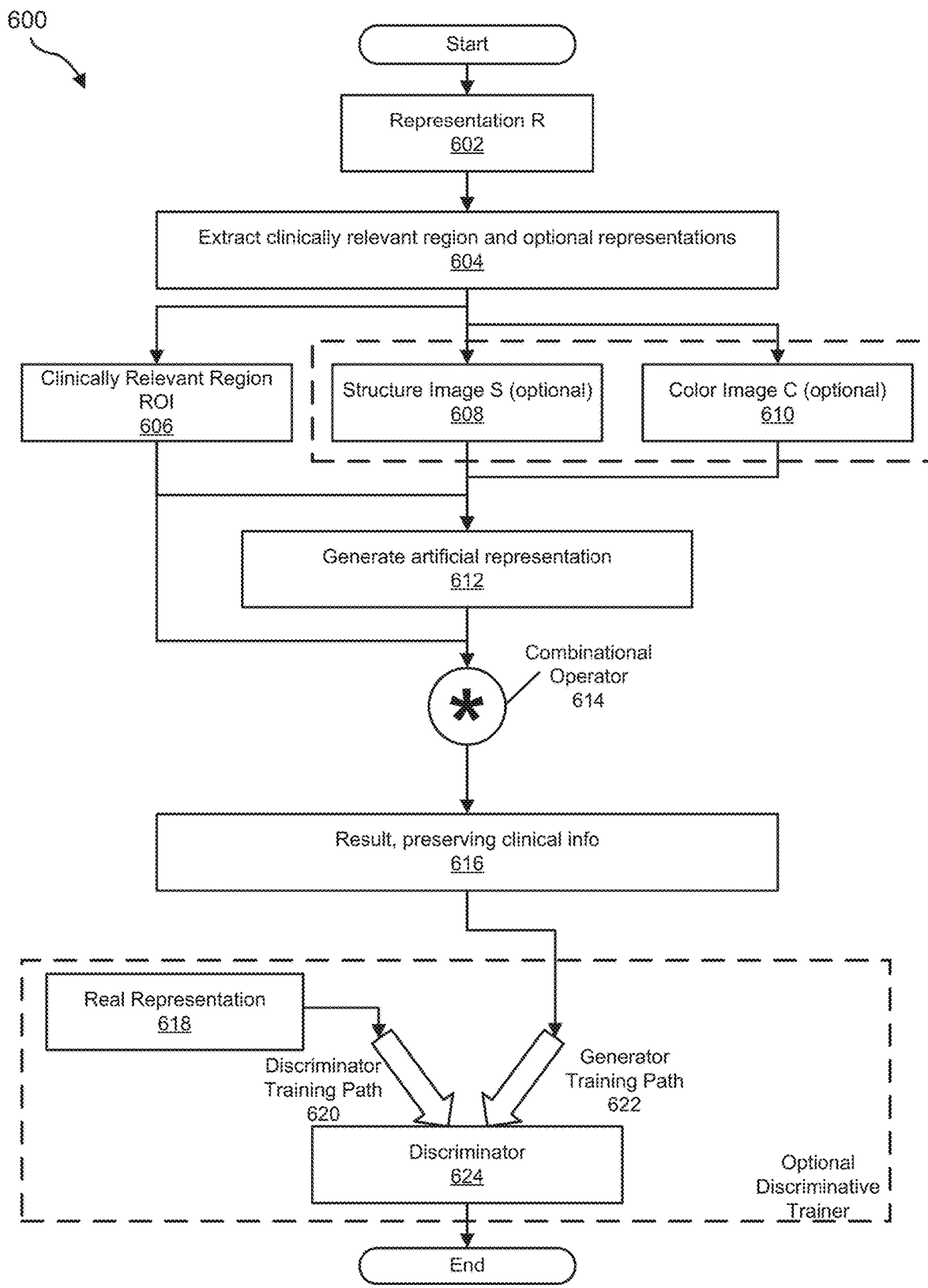
FIG. 6 shows a dataflow diagram of an example dataflow for anonymizing clinical data, in accordance with some embodiments.

FIG. 6 is a dataflow diagram of an example computer-implemented dataflow 600 for anonymizing clinical data. The steps shown in FIG. 6 may be performed by any suitable computer-executable code and/or computing system, including system 100 in FIG. 1, system 200 in FIG. 2, and/or variations or combinations of one or more of the same. In one example, each of the steps shown in FIG. 6 may represent an algorithm whose structure includes and/or is represented by multiple sub-steps, examples of which will be provided in greater detail below. Dataflow 600 illustrates an example implementation utilizing a generative adversarial network (GAN).

A GAN may utilize two separate machine learning (e.g., neural network) modules, a generator and a discriminator. The generator may be trained, using a dataset of relevant representation data (e.g., images), to generate realistic representation data of body parts. The generator may be further trained to reproduce the original representation data by determining a loss, using any appropriate loss function (e.g., L1 or Wasserstein), from the original representation data to the resulting representation data and back-propagating the gradient of the loss through the neural network. The back-propagation may adjust the neural network's parameters to minimize the loss.

A discriminator may process representation data to classify the input as "real" (e.g., appears genuine as if captured from the real world) or "generated" (e.g., appears to be artificially generated). The discriminator may be trained using datasets of known real representations and generated representations. The generator may then be trained to "fool" (e.g., have the discriminator classify a generated representation as a real representation) the discriminator.

The discriminator's weights may be fixed such that the discriminator is not learning while training the generator. The error of fooling the discriminator (e.g., a negative of the discriminator loss) may be back-propagated through the generator to adjust the generator's weights in order to improve the realism of the generator's output.

As illustrated in FIG. 6, at block 602, representation R, which may correspond to representation data 122, may be provided. For example, receiving module 104 may, as part of computing device 202 and/or server 206 in FIG. 2, receive representation R.

At block 604, one or more of the systems described herein may extract a clinically relevant region and optional representations. For example, extracting module 106 may, as part of computing device 202 and/or server 206 in FIG. 2, extract clinically relevant region ROI, which may correspond to clinical representation data 124, from representation R at block 606. Extracting module 106 may also optionally extract structure image S, which may correspond to structure representation 132, from representation R at block 608. Extracting module 106 may also optionally extract color image C, which may correspond to color representation 134, from representation R at block 610.

At block 612, one or more of the systems described herein may generate an artificial representation. The generator may correspond to generating module 108. For example, generating module 108 may, as part of computing device 202 and/or server 206 in FIG. 2, generate the artificial representation using clinically relevant region ROI, structure image S, and color image C as inputs. Subsequently, the artificial representation may be combined with clinically relevant region ROI with combinational operator 614, which may include, for instance, simple replacement, averaging values, alpha channel blurring, Gaussian alpha channel blurring, etc. The result, which preserves clinical information, at block 616 may anonymize the patient. The result may also fool the discriminator of the GAN.

FIG. 6 further illustrates an optional discriminative trainer portion. The result 616, as the result of the generator, may continue with generator training path 622 to discriminator 624, which may correspond to generating module 108. As described above, discriminator 624 may be trained, via discriminator training path 620, using real representation 618. The generator may also be trained, via generator training path 622, to fool the discriminator.

In some implementations, the generator may be temporally aware in order to maintain temporal coherence for video or 3D video. For example, multiple frames of the source representation data and past reconstructed representations may be input into the generator. An additional discriminator may validate temporal coherence of the frames. Video may be generated by first creating a single frame and enforcing temporal coherence at subsequent times via the discriminator. Alternatively, the video may be generated from a single image and a series of poses. The generator may learn meta-information associated with modeling a pose into video. The generator may then generate a single image or 3D image, and represent that image transitioning through the series of poses using the meta-information.

In some implementations, before and after images may be created as short, two-frame video segments. The artificial representation data may remain constant for the two frames. The clinical representation data for before treatment and after treatment may then be embedded into or otherwise incorporated with the artificial representation data.

As explained above, a treatment professional may take photos of a patient's face and head. The anonymization methods and apparatus as described herein may receive the photos and identify the mouth for preservation. The anonymization methods and apparatus as described herein may artificially generate a face, which may look realistic and share non-identifiable features of the original face. The anonymization methods and apparatus may then embed the original mouth into the artificial face to create a realistic and aesthetically pleasing face. The anonymized face may maintain the mouth features for the treatment professional to observe, but may keep the patient's identity hidden. The anonymized face may preserve more information and be less distracting than conventional black-out or cropped facial images.

The anonymization methods and apparatus may be used to demonstrate smile examples or treatment planning examples. For instance, the anonymization methods and apparatus may support online smile galleries, be shown at dental conventions, be implemented as a mobile application, or be developed as a teaching tool.

The anonymization methods and apparatus may be used for researcher surveys. For example, consumers, general practitioners, and orthodontic professionals may be presented with anonymized photos to research smile properties (e.g., smile aesthetics, smile outcomes, etc.). The same smile may be presented in different facial contexts, such as across different ethnicities. Alternatively, the teeth may change (e.g., changing the midline, size of lateral incisor, etc.) and the face may stay the same.

Although the systems and methods are described above with respect to orthodontic treatment, in other implementations, the anonymization methods and apparatus may be used for other medical contexts, such as plastic surgery. Alternatively, the anonymization methods and apparatus may be used outside of medical contexts, such as for generating avatars, concealing minors' identities for publishing, etc. In such contexts, the clinically relevant region may correspond to or be defined by important body features relevant to the given context.

Figure 7:
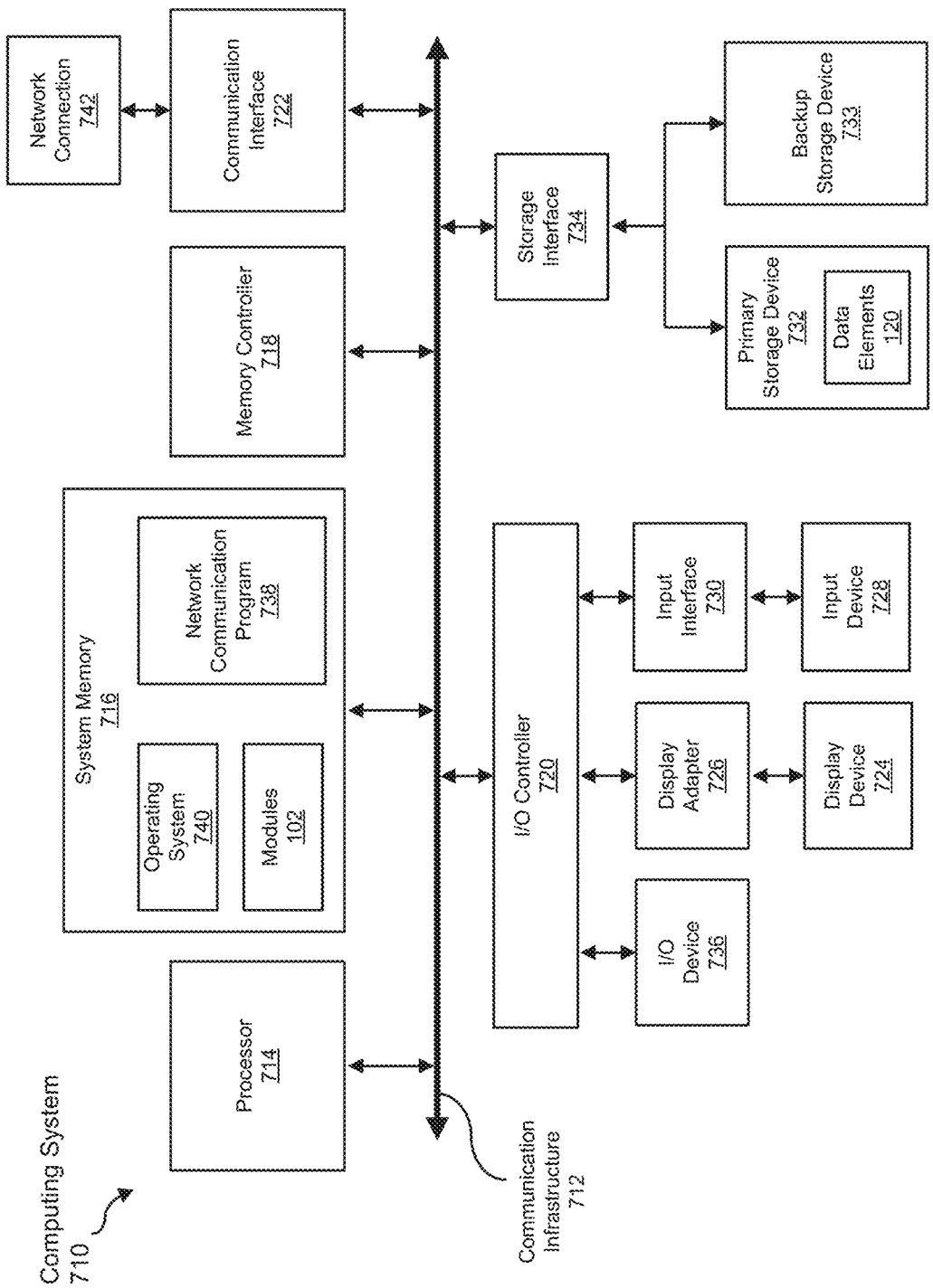
FIG. 7 shows a block diagram of an example computing system capable of implementing one or more embodiments described and/or illustrated herein, in accordance with some embodiments.

FIG. 7 is a block diagram of an example computing system 710 capable of implementing one or more of the embodiments described and/or illustrated herein. For example, all or a portion of computing system 710 may perform and/or be a means for performing, either alone or in combination with other elements, one or more of the steps described herein (such as one or more of the steps illustrated in FIG. 3). All or a portion of computing system 710 may also perform and/or be a means for performing any other steps, methods, or processes described and/or illustrated herein.

Computing system 710 broadly represents any single or multi-processor computing device or system capable of executing computer-readable instructions. Examples of computing system 710 include, without limitation, workstations, laptops, client-side terminals, servers, distributed computing systems, handheld devices, or any other computing system or device. In its most basic configuration, computing system 710 may include at least one processor 714 and a system memory 716.

Processor 714 generally represents any type or form of physical processing unit (e.g., a hardware-implemented central processing unit) capable of processing data or interpreting and executing instructions. In certain embodiments, processor 714 may receive instructions from a software application or module. These instructions may cause processor 714 to perform the functions of one or more of the example embodiments described and/or illustrated herein.

System memory 716 generally represents any type or form of volatile or non-volatile storage device or medium capable of storing data and/or other computer-readable instructions. Examples of system memory 716 include, without limitation, Random Access Memory (RAM), Read Only Memory (ROM), flash memory, or any other suitable memory device. Although not required, in certain embodiments computing system 710 may include both a volatile memory unit (such as, for example, system memory 716) and a non-volatile storage device (such as, for example, primary storage device 732, as described in detail below). In one example, one or more of modules 102 from FIG. 1 may be loaded into system memory 716.

In some examples, system memory 716 may store and/or load an operating system 740 for execution by processor 714. In one example, operating system 740 may include and/or represent software that manages computer hardware and software resources and/or provides common services to computer programs and/or applications on computing system 710. Examples of operating system 740 include, without limitation, LINUX, JUNOS, MICROSOFT WINDOWS, WINDOWS MOBILE, MAC OS, APPLE'S IOS, UNIX, GOOGLE CHROME OS, GOOGLE'S ANDROID, SOLARIS, variations of one or more of the same, and/or any other suitable operating system.

In certain embodiments, example computing system 710 may also include one or more components or elements in addition to processor 714 and system memory 716. For example, as illustrated in FIG. 7, computing system 710 may include a memory controller 718, an Input/Output (I/O) controller 720, and a communication interface 722, each of which may be interconnected via a communication infrastructure 712. Communication infrastructure 712 generally represents any type or form of infrastructure capable of facilitating communication between one or more components of a computing device. Examples of communication infrastructure 712 include, without limitation, a communication bus (such as an Industry Standard Architecture (ISA), Peripheral Component Interconnect (PCI), PCI Express (PCIe), or similar bus) and a network.

Memory controller 718 generally represents any type or form of device capable of handling memory or data or controlling communication between one or more components of computing system 710. For example, in certain embodiments memory controller 718 may control communication between processor 714, system memory 716, and I/O controller 720 via communication infrastructure 712.

I/O controller 720 generally represents any type or form of module capable of coordinating and/or controlling the input and output functions of a computing device. For example, in certain embodiments I/O controller 720 may control or facilitate transfer of data between one or more elements of computing system 710, such as processor 714, system memory 716, communication interface 722, display adapter 726, input interface 730, and storage interface 734.

As illustrated in FIG. 7, computing system 710 may also include at least one display device 724 coupled to I/O controller 720 via a display adapter 726. Display device 724 generally represents any type or form of device capable of visually displaying information forwarded by display adapter 726. Similarly, display adapter 726 generally represents any type or form of device configured to forward graphics, text, and other data from communication infrastructure 712 (or from a frame buffer, as known in the art) for display on display device 724.

As illustrated in FIG. 7, example computing system 710 may also include at least one input device 728 coupled to I/O controller 720 via an input interface 730. Input device 728 generally represents any type or form of input device capable of providing input, either computer or human generated, to example computing system 710. Examples of input device 728 include, without limitation, a keyboard, a pointing device, a speech recognition device, variations or combinations of one or more of the same, and/or any other input device.

Additionally or alternatively, example computing system 710 may include additional I/O devices. For example, example computing system 710 may include I/O device 736. In this example, I/O device 736 may include and/or represent a user interface that facilitates human interaction with computing system 710. Examples of I/O device 736 include, without limitation, a computer mouse, a keyboard, a monitor, a printer, a modem, a camera, a scanner, a microphone, a touchscreen device, variations or combinations of one or more of the same, and/or any other I/O device.

Communication interface 722 broadly represents any type or form of communication device or adapter capable of facilitating communication between example computing system 710 and one or more additional devices. For example, in certain embodiments communication interface 722 may facilitate communication between computing system 710 and a private or public network including additional computing systems. Examples of communication interface 722 include, without limitation, a wired network interface (such as a network interface card), a wireless network interface (such as a wireless network interface card), a modem, and any other suitable interface. In at least one embodiment, communication interface 722 may provide a direct connection to a remote server via a direct link to a network, such as the Internet. Communication interface 722 may also indirectly provide such a connection through, for example, a local area network (such as an Ethernet network), a personal area network, a telephone or cable network, a cellular telephone connection, a satellite data connection, or any other suitable connection.

In certain embodiments, communication interface 722 may also represent a host adapter configured to facilitate communication between computing system 710 and one or more additional network or storage devices via an external bus or communications channel. Examples of host adapters include, without limitation, Small Computer System Interface (SCSI) host adapters, Universal Serial Bus (USB) host adapters, Institute of Electrical and Electronics Engineers (IEEE) 1394 host adapters, Advanced Technology Attachment (ATA), Parallel ATA (PATA), Serial ATA (SATA), and External SATA (eSATA) host adapters, Fibre Channel interface adapters, Ethernet adapters, or the like. Communication interface 722 may also allow computing system 710 to engage in distributed or remote computing. For example, communication interface 722 may receive instructions from a remote device or send instructions to a remote device for execution.

In some examples, system memory 716 may store and/or load a network communication program 738 for execution by processor 714. In one example, network communication program 738 may include and/or represent software that enables computing system 710 to establish a network connection 742 with another computing system (not illustrated in FIG. 7) and/or communicate with the other computing system by way of communication interface 722. In this example, network communication program 738 may direct the flow of outgoing traffic that is sent to the other computing system via network connection 742. Additionally or alternatively, network communication program 738 may direct the processing of incoming traffic that is received from the other computing system via network connection 742 in connection with processor 714.

Although not illustrated in this way in FIG. 7, network communication program 738 may alternatively be stored and/or loaded in communication interface 722. For example, network communication program 738 may include and/or represent at least a portion of software and/or firmware that is executed by a processor and/or Application Specific Integrated Circuit (ASIC) incorporated in communication interface 722.

As illustrated in FIG. 7, example computing system 710 may also include a primary storage device 732 and a backup storage device 733 coupled to communication infrastructure 712 via a storage interface 734. Storage devices 732 and 733 generally represent any type or form of storage device or medium capable of storing data and/or other computer-readable instructions. For example, storage devices 732 and 733 may be a magnetic disk drive (e.g., a so-called hard drive), a solid state drive, a floppy disk drive, a magnetic tape drive, an optical disk drive, a flash drive, or the like. Storage interface 734 generally represents any type or form of interface or device for transferring data between storage devices 732 and 733 and other components of computing system 710. In one example, data elements 120 from FIG. 1 may be stored and/or loaded in primary storage device 732.

In certain embodiments, storage devices 732 and 733 may be configured to read from and/or write to a removable storage unit configured to store computer software, data, or other computer-readable information. Examples of suitable removable storage units include, without limitation, a floppy disk, a magnetic tape, an optical disk, a flash memory device, or the like. Storage devices 732 and 733 may also include other similar structures or devices for allowing computer software, data, or other computer-readable instructions to be loaded into computing system 710. For example, storage devices 732 and 733 may be configured to read and write software, data, or other computer-readable information. Storage devices 732 and 733 may also be a part of computing system 710 or may be a separate device accessed through other interface systems.

Many other devices or subsystems may be connected to computing system 710. Conversely, all of the components and devices illustrated in FIG. 7 need not be present to practice the embodiments described and/or illustrated herein. The devices and subsystems referenced above may also be interconnected in different ways from that shown in FIG. 7. Computing system 710 may also employ any number of software, firmware, and/or hardware configurations. For example, one or more of the example embodiments disclosed herein may be encoded as a computer program (also referred to as computer software, software applications, computer-readable instructions, or computer control logic) on a computer-readable medium. The term "computer-readable medium," as used herein, generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

The computer-readable medium containing the computer program may be loaded into computing system 710. All or a portion of the computer program stored on the computer-readable medium may then be stored in system memory 716 and/or various portions of storage devices 732 and 733. When executed by processor 714, a computer program loaded into computing system 710 may cause processor 714 to perform and/or be a means for performing the functions of one or more of the example embodiments described and/or illustrated herein. Additionally or alternatively, one or more of the example embodiments described and/or illustrated herein may be implemented in firmware and/or hardware. For example, computing system 710 may be configured as an Application Specific Integrated Circuit (ASIC) adapted to implement one or more of the example embodiments disclosed herein.

Figure 8:
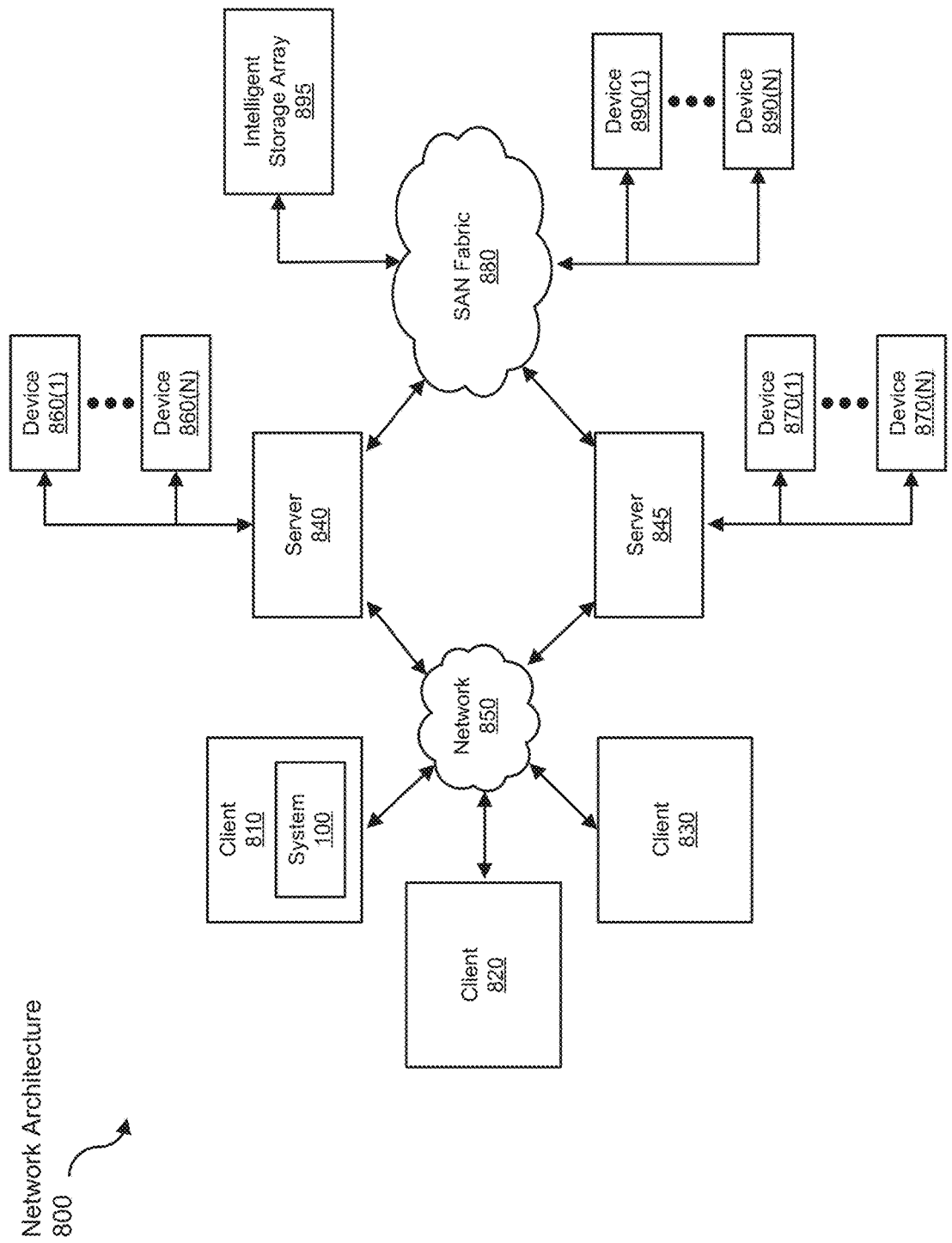
FIG. 8 shows a block diagram of an example computing network capable of implementing one or more of the embodiments described and/or illustrated herein, in accordance with some embodiments.

FIG. 8 is a block diagram of an example network architecture 800 in which client systems 810, 820, and 830 and servers 840 and 845 may be coupled to a network 850. As detailed above, all or a portion of network architecture 800 may perform and/or be a means for performing, either alone or in combination with other elements, one or more of the steps disclosed herein (such as one or more of the steps illustrated in FIG. 3). All or a portion of network architecture 800 may also be used to perform and/or be a means for performing other steps and features set forth in the instant disclosure.

Client systems 810, 820, and 830 generally represent any type or form of computing device or system, such as example computing system 710 in FIG. 7. Similarly, servers 840 and 845 generally represent computing devices or systems, such as application servers or database servers, configured to provide various database services and/or run certain software applications. Network 850 generally represents any telecommunication or computer network including, for example, an intranet, a WAN, a LAN, a PAN, or the Internet. In one example, client systems 810, 820, and/or 830 and/or servers 840 and/or 845 may include all or a portion of system 100 from FIG. 1.

As illustrated in FIG. 8, one or more storage devices 860(1)-(N) may be directly attached to server 840. Similarly, one or more storage devices 870(1)-(N) may be directly attached to server 845. Storage devices 860(1)-(N) and storage devices 870(1)-(N) generally represent any type or form of storage device or medium capable of storing data and/or other computer-readable instructions. In certain embodiments, storage devices 860(1)-(N) and storage devices 870(1)-(N) may represent Network-Attached Storage (NAS) devices configured to communicate with servers 840 and 845 using various protocols, such as Network File System (NFS), Server Message Block (SMB), or Common Internet File System (CIFS).

Servers 840 and 845 may also be connected to a Storage Area Network (SAN) fabric 880. SAN fabric 880 generally represents any type or form of computer network or architecture capable of facilitating communication between a plurality of storage devices. SAN fabric 880 may facilitate communication between servers 840 and 845 and a plurality of storage devices 890(1)-(N) and/or an intelligent storage array 895. SAN fabric 880 may also facilitate, via network 850 and servers 840 and 845, communication between client systems 810, 820, and 830 and storage devices 890(1)-(N) and/or intelligent storage array 895 in such a manner that devices 890(1)-(N) and array 895 appear as locally attached devices to client systems 810, 820, and 830. As with storage devices 860(1)-(N) and storage devices 870(1)-(N), storage devices 890(1)-(N) and intelligent storage array 895 generally represent any type or form of storage device or medium capable of storing data and/or other computer-readable instructions.

In certain embodiments, and with reference to example computing system 710 of FIG. 7, a communication interface, such as communication interface 722 in FIG. 7, may be used to provide connectivity between each client system 810, 820, and 830 and network 850. Client systems 810, 820, and 830 may be able to access information on server 840 or 845 using, for example, a web browser or other client software. Such software may allow client systems 810, 820, and 830 to access data hosted by server 840, server 845, storage devices 860(1)-(N), storage devices 870(1)-(N), storage devices 890(1)-(N), or intelligent storage array 895. Although FIG. 8 depicts the use of a network (such as the Internet) for exchanging data, the embodiments described and/or illustrated herein are not limited to the Internet or any particular network-based environment.

In at least one embodiment, all or a portion of one or more of the example embodiments disclosed herein may be encoded as a computer program and loaded onto and executed by server 840, server 845, storage devices 860(1)-(N), storage devices 870(1)-(N), storage devices 890(1)-(N), intelligent storage array 895, or any combination thereof. All or a portion of one or more of the example embodiments disclosed herein may also be encoded as a computer program, stored in server 840, run by server 845, and distributed to client systems 810, 820, and 830 over network 850.

As detailed above, computing system 710 and/or one or more components of network architecture 800 may perform and/or be a means for performing, either alone or in combination with other elements, one or more steps of an example method for anonymizing clinical data.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered example in nature since many other architectures can be implemented to achieve the same functionality.

In some examples, all or a portion of example system 100 in FIG. 1 may represent portions of a cloud-computing or network-based environment. Cloud-computing environments may provide various services and applications via the Internet. These cloud-based services (e.g., software as a service, platform as a service, infrastructure as a service, etc.) may be accessible through a web browser or other remote interface. Various functions described herein may be provided through a remote desktop environment or any other cloud-based computing environment.

In various embodiments, all or a portion of example system 100 in FIG. 1 may facilitate multi-tenancy within a cloud-based computing environment. In other words, the software modules described herein may configure a computing system (e.g., a server) to facilitate multi-tenancy for one or more of the functions described herein. For example, one or more of the software modules described herein may program a server to enable two or more clients (e.g., customers) to share an application that is running on the server. A server programmed in this manner may share an application, operating system, processing system, and/or storage system among multiple customers (i.e., tenants). One or more of the modules described herein may also partition data and/or configuration information of a multi-tenant application for each customer such that one customer cannot access data and/or configuration information of another customer.

According to various embodiments, all or a portion of example system 100 in FIG. 1 may be implemented within a virtual environment. For example, the modules and/or data described herein may reside and/or execute within a virtual machine. As used herein, the term "virtual machine" generally refers to any operating system environment that is abstracted from computing hardware by a virtual machine manager (e.g., a hypervisor). Additionally or alternatively, the modules and/or data described herein may reside and/or execute within a virtualization layer. As used herein, the term "virtualization layer" generally refers to any data layer and/or application layer that overlays and/or is abstracted from an operating system environment. A virtualization layer may be managed by a software virtualization solution (e.g., a file system filter) that presents the virtualization layer as though it were part of an underlying base operating system. For example, a software virtualization solution may redirect calls that are initially directed to locations within a base file system and/or registry to locations within a virtualization layer.

In some examples, all or a portion of example system 100 in FIG. 1 may represent portions of a mobile computing environment. Mobile computing environments may be implemented by a wide range of mobile computing devices, including mobile phones, tablet computers, e-book readers, personal digital assistants, wearable computing devices (e.g., computing devices with a head-mounted display, smartwatches, etc.), and the like. In some examples, mobile computing environments may have one or more distinct features, including, for example, reliance on battery power, presenting only one foreground application at any given time, remote management features, touchscreen features, location and movement data (e.g., provided by Global Positioning Systems, gyroscopes, accelerometers, etc.), restricted platforms that restrict modifications to system-level configurations and/or that limit the ability of third-party software to inspect the behavior of other applications, controls to restrict the installation of applications (e.g., to only originate from approved application stores), etc. Various functions described herein may be provided for a mobile computing environment and/or may interact with a mobile computing environment.

In addition, all or a portion of example system 100 in FIG. 1 may represent portions of, interact with, consume data produced by, and/or produce data consumed by one or more systems for information management. As used herein, the term "information management" may refer to the protection, organization, and/or storage of data. Examples of systems for information management may include, without limitation, storage systems, backup systems, archival systems, replication systems, high availability systems, data search systems, virtualization systems, and the like.

In some embodiments, all or a portion of example system 100 in FIG. 1 may represent portions of, produce data protected by, and/or communicate with one or more systems for information security. As used herein, the term "information security" may refer to the control of access to protected data. Examples of systems for information security may include, without limitation, systems providing managed security services, data loss prevention systems, identity authentication systems, access control systems, encryption systems, policy compliance systems, intrusion detection and prevention systems, electronic discovery systems, and the like.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising."

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

The present disclosure includes the following numbered clauses.

Clause 1. A method of anonymizing clinical data comprising: receiving representation data corresponding to a body part, the representation data comprising a clinically relevant region and an anonymization region; extracting, from the representation data, clinical representation data corresponding to the clinically relevant region of the representation data; generating artificial representation data corresponding to the anonymization region of the representation data; and creating, based at least on the clinical representation data and the artificial representation data, anonymized representation data that substantially preserves the clinically relevant region.

Clause 2. The method of clause 1, wherein the artificial representation comprises a photo-realistic image.

Clause 3. The method of clause 2, wherein the photo-realistic image comprises an output color image and the anonymization region comprises a color image.

Clause 4. The method of clause 2, wherein the photo-realistic image comprises a two-dimensional image.

Clause 5. The method of clause 2, wherein the photo-realistic image comprises a two-dimensional image generated from the two-dimensional anonymization region.

Clause 6. The method of clause 2, wherein the photo-realistic image corresponds to a two-dimensional anonymization region.

Clause 7. The method of clause 1, wherein creating, based at least on the clinical representation data and the artificial representation data, anonymized representation data that substantially preserves the clinically relevant region, comprises combining the clinically relevant region with the anonymized representation data.

Clause 8. The method of clause 1, wherein the clinical representation data comprises a fidelity loss of no more than 10% with respect to the clinically relevant region and the artificial representation data comprise a fidelity loss of 30% or more with respect to the anonymization region of the representation data.

Clause 9. The method of clause 8, wherein the fidelity loss of the clinical representation corresponds to at least one of an L1 loss, a least absolute deviations (LAD) loss, and a least absolute errors (LAE) loss.

Clause 10. The method of clause 8, wherein the fidelity loss of the anonymization region corresponds to at least one of an L1 loss, a least absolute deviations (LAD) loss, and a least absolute errors (LAE) loss.

Clause 11. The method of clause 1, further comprising comparing the anonymization region to the artificial representation to confirm sufficient anonymization of the artificial representation.

Clause 12. The method of clause 1, wherein the artificial representation comprises a contrast of at least 50% between a maximum intensity pixel of the artificial representation and a minimum intensity pixel of the artificial representation.

Clause 13. The method of clause 12, wherein the artificial representation region comprises a plurality of red pixels, a plurality of blue pixels and a plurality of green pixels and wherein the contrast comprises at least 50% for each of the plurality of red pixels, the plurality of blue pixels, and the plurality of green pixels.

Clause 14. The method of clause 1, wherein the anonymization region comprises a first power spectrum distribution of spatial frequencies and the artificial representation comprises a second power spectrum distribution of special frequencies and wherein the first power spectrum distribution of spatial frequencies comprise a first amount of spectral power between a Nyquist sampling frequency and half of the Nyquist sampling frequency and the second power spectrum distribution comprises a second amount of spectral power between the Nyquist frequency and half of the Nyquist frequency and wherein the second amount differs from the first amount by no more than about 50% of the first amount and optionally no more than about 25%.

Clause 15. The method of clause 1, wherein extracting the clinical representation data further comprises: determining key points of the body part from the representation data; identifying key points corresponding to the clinically relevant region; and selecting sub-representation data from the representation data based on the identified key points.

Clause 16. The method of clause 15, wherein the key points correspond to facial landmarks.

Clause 17. The method of clause 15, wherein the key points correspond to Baumrind landmarks.

Clause 18. The method of clause 15, wherein the key points include about 30 to about 150 landmarks.

Clause 19. The method of clause 15, wherein the key points include 68 landmarks.

Clause 20. The method of clause 1, further comprising creating a structure representation corresponding to a shape and pose of the body part.

Clause 21. The method of clause 20, wherein the structure representation is determined based on key points of the body part.

Clause 22. The method of clause 21, wherein the structure representation includes connected key points.

Clause 23. The method of clause 21, wherein the structure representation includes a polygon formed from connected key points.

Clause 24. The method of clause 20, wherein the structure representation is based on edge detection of the representation data.

Clause 25. The method of clause 20, wherein the anonymized representation data is created based on the structure representation.

Clause 26. The method of clause 1, further comprising creating a color representation indicating one or more colors of one or more regions of the body part.

Clause 27. The method of clause 26, wherein the color representation preserves the one or more colors and obscures a structure of the body part.

Clause 28. The method of clause 25, wherein the color representation is created using a Gaussian blur or a piecewise non-linear function.

Clause 29. The method of clause 26, wherein the color representation is crated using image data adjacent the clinically relevant region.

Clause 30. The method of clause 26, wherein the color representation is crated using image data within the clinically relevant region.

Clause 31. The method of clause 1, wherein the color representation is in the LAB color space.

Clause 32. The method of clause 1, wherein the body part comprises a face of the patient and the anonymization region comprises eyes of the face and the clinically relevant region comprises a mouth of the face.

Clause 33. The method of clause 1, wherein the clinically relevant region comprises the mouth opening and lips of the patient.

Clause 34. The method of clause 33, wherein the clinically relevant region does not comprise the eyes of the patient.

Clause 35. The method of clause 1, wherein the clinically relevant region comprises the mouth opening of the patient.

Clause 36. The method of clause 35, wherein the clinically relevant region does not comprise the eyes of the patient.

Clause 37. The method of clause 1, wherein the clinically relevant region is associated with a mandibular advancement treatment.

Clause 38. The method of clause 37, wherein the clinically relevant region includes a pogonion identified from the body part.

Clause 39. The method of clause 1, wherein the clinically relevant region is associated with a cleft lip treatment.

Clause 40. The method of clause 39, wherein the clinically relevant region includes a facial deformity.

Clause 41. The method of clause 40, wherein the facial deformity includes at least one of a cleft lip, cleft palate, facial injury, and dental trauma.

Clause 42. The method of clause 1, wherein the clinically relevant region is associated with a deep bite treatment.

Clause 43. The method of clause 42, wherein the clinically relevant region includes a relationship between an upper jaw and a lower jaw identified from the body part.

Clause 44. The method of clause 1, wherein the clinically relevant region is associated with a palatal expansion treatment.

Clause 45. The method of clause 44, wherein the clinically relevant region includes a horizontal face width.

Clause 46. The method of clause 1, wherein the clinically relevant region is associated with a class II malocclusion treatment.

Clause 47. The method of clause 46, wherein the clinically relevant region includes upper and lower dental archforms.

Clause 48. The method of clause 1, wherein the clinically relevant region is associated with a midline shift.

Clause 49. The method of clause 48, wherein the clinically relevant region includes a philtrum.

Clause 50. The method of clause 1, wherein the clinically relevant region is associated with soft tissue changes.

Clause 51. The method of clause 50, wherein the clinically relevant region includes a soft tissue facial landmark.

Clause 52. The method of clause 51, wherein the soft tissue facial landmark includes at least one of a pogonion, a soft tissue end point, and a result of soft tissue analysis.

Clause 53. The method of clause 1, wherein the anonymized representation data comprises video data.

Clause 54. The method of clause 1, wherein the anonymized representation data comprises three-dimensional (3D) data.

Clause 55. The method of clause 1, wherein creating the anonymized representation data further comprises: creating, based at least on the clinical representation data and the artificial representation data, a first frame corresponding to the body part in a pose; and creating a second frame corresponding to the body part transitioning the pose to another pose.

Clause 56. The method of clause 1, wherein creating the anonymized representation data further comprises using a generative adversarial network (GAN).

Clause 57. The method of clause 57, wherein the GAN creates the anonymized representation data based on the clinically relevant data and key points of the body part from the representation data.

Clause 58. The method of clause 58, wherein the GAN creates the anonymized representation data based on the clinically relevant data and a mask generated based on key points of the body part from the representation data.

Clause 59. The method of clause 58, wherein the GAN receives the clinically relevant data and a mask as inputs.

Clause 60. The method of clause 57, wherein the mask is a multi-channel mask.

Clause 61. The method of clause 60, wherein the multi-channel mask comprises one or more of an eyebrow mask, nose mask, lips mask, mouth opening mask, a jaw line mask, and a face mask.

Clause 62. The method of clause 60, wherein the multi-channel mask is a seven-channel mask.

Clause 63. The method of clause 60, wherein the multi-channel mask comprises seven masks.

Clause 64. The method of clause 56, wherein creating the anonymized representation data further comprises creating a plurality of frames, wherein the GAN enforces temporal coherence between the plurality of frames.

Clause 65. The method of any of clauses 59-64, wherein creating, based at least on the clinical representation data and the artificial representation data, anonymized representation data that substantially preserves the clinically relevant region, comprises combining the clinically relevant region corresponding to a mask of the mouth with the anonymized representation data.

Clause 66. The method of clause 65, wherein the anonymized representation data corresponds to one or more masks of one or more of eyes, nose, eyebrows, and jaw line.

Clause 67. The method of clause 65, wherein the anonymized representation data corresponds to mask channels for two eyes, two eyebrows, a nose, and a jaw line.

Clause 68. The method of clause 65, wherein the clinically relevant region further corresponds to a mask of the lips.

Clause 69. A system comprising a processor and/or memory configured with instructions to perform the method of any one of the preceding claims.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof

What is claimed is:
1. A method of anonymizing clinical data comprising:
receiving an image of a facial region, wherein the image of the facial region includes: respective shapes and locations of original anatomical features of the facial region, a clinically relevant region corresponding to an oral cavity and an anonymization region outside the oral cavity;
extracting, by one or more processors, from the image, clinical representation data, wherein the clinical representation data: corresponds to the clinically relevant region and includes one or more of the original anatomical features of the facial region;
generating, by one or more processors, structure representation data for the original anatomical features, wherein the structure representation data defines the respective shape and locations of the original anatomical features;
using the structure representation data and a trained generative adversarial network (GAN) to generate, by one or more processors, artificial representation data corresponding to the anonymization region wherein the GAN is trained to generate photorealistic representations of the anonymization region; and using the clinical representation data and the artificial representation data to create, by one or more processors, an anonymized representation of the facial region including anonymized anatomical features having the shape and the location of the original anatomical features in the anonymization region of the representation data and the clinical representation data including original anatomical features within the clinically relevant region.

2. The method of claim 1, wherein the artificial representation comprises a photo-realistic image.

3. The method of claim 2, wherein the photo-realistic image comprises an output color image and the anonymization region comprises a color image.

4. The method of claim 2, wherein the photo-realistic image comprises a two-dimensional image.

5. The method of claim 2, wherein the photo-realistic image comprises a two-dimensional image generated from the two-dimensional anonymization region.

6. The method of claim 2, wherein the photo-realistic image corresponds to a two-dimensional anonymization region.

7. The method of claim 1, wherein creating, based at least on the clinical representation data and the artificial representation data, anonymized representation data, comprises combining the clinically relevant region with the anonymized representation data.

8. A method of anonymizing clinical data comprising:
receiving representation data of a facial region and including respective shapes and poses of original anatomical features of the original body part, the representation data comprising a clinically relevant region comprising at least a portion of an oral cavity of a patient and an anonymization region outside the oral cavity;
determining, by one or more processors, locations of first points of the original body part representative of the respective shape and pose of the original anatomical features of the original body part from the representation data;
determining, by one or more processors, locations of second points corresponding to the clinically relevant region; and
selecting, by one or more processors, sub-representation data of the clinical representation data corresponding to the clinically relevant region from the representation data based on the locations of the second points;
extracting, by one or more processors, from the representation data, the clinical representation data within the selected sub-representation area;
generating, by one or more processors, artificial representation data of artificial anatomical features within the anonymization region using the locations of the first points of the original body part representative of the shape and pose of the original anatomical features of the body part within the anonymization region, the artificial anatomical features having the shape and post of the original anatomical features; and
creating, based at least on the clinical representation data and the artificial representation data of artificial anatomical features within the anonymization region, anonymized representation of the facial region including anonymized anatomical features having the shape and the location of the original anatomical features in the anonymization region of the representation data and the clinical representation data including original anatomical features within the clinically relevant region.

9. The method of claim 8, wherein the locations of the first and second points correspond to locations of facial landmarks.

10. The method of claim 8, further comprising creating a structure representation including a polygon formed from connecting the first points had having an outline and a shape and pose of the using the original anatomical features.

11. The method of claim 8, further comprising creating a color representation including one or more colors of one or more regions of the body part; wherein a color of the artificial anatomical features is based on the color representation data.

12. The method of claim 11, wherein the color representation is created using a Gaussian blur or a piecewise non-linear function.

13. The method of claim 12, wherein the color representation is created using image data within the clinically relevant region.

14. A system of anonymizing clinical data comprising:
a processor configured with instructions to cause the system to:
receive representation data of a facial region and including respective shapes and poses of original anatomical features of the body part, the representation data comprising a clinically relevant region and an anonymization region;
extract, from the representation data, clinical representation data corresponding to the clinically relevant region of the representation data;
generate artificial representation data corresponding to the anonymization region of the representation data including the respective location, and pose of respective original anatomical features of the body part in the representation data; and
use a generative adversarial network to create, based at least on the clinical representation data and the artificial representation data, anonymized representation of the facial region including anonymized anatomical features having the shape and the location of the original anatomical features in the anonymization region of the representation data and the clinical representation data including original anatomical features within the clinically relevant region.

15. The system of claim 14, wherein the clinically relevant region comprises the mouth opening of the patient.

16. The system of claim 14, wherein the GAN creates the anonymized representation data based on the clinically relevant data and points of the body part from the representation data.

17. The system of claim 16, wherein the GAN creates the anonymized representation data based on the clinically relevant data and a mask generated based on points of the body part from the representation data.

18. The system of claim 17, wherein the mask is a multi-channel mask.

19. The method of claim 1, wherein the portion of the oral cavity comprises a dentition of the patient.

* * * * *